United States Patent
Wang

(10) Patent No.: US 11,143,730 B2
(45) Date of Patent: Oct. 12, 2021

(54) SYSTEM AND METHOD FOR PARALLEL MAGNETIC RESONANCE IMAGING

(71) Applicant: University of Cincinnati, Cincinnati, OH (US)

(72) Inventor: Jinghua Wang, Mason, OH (US)

(73) Assignee: UNIVERSITY OF CINCINNATI, Cincinnati, OH (US)

( * ) Notice: Subject to any disclaimer, the term of this patent is extended or adjusted under 35 U.S.C. 154(b) by 15 days.

(21) Appl. No.: 16/841,020

(22) Filed: Apr. 6, 2020

(65) Prior Publication Data

US 2020/0319283 A1    Oct. 8, 2020

Related U.S. Application Data

(60) Provisional application No. 62/829,676, filed on Apr. 5, 2019.

(51) Int. Cl.
| | |
|---|---|
| *G01R 33/561* | (2006.01) |
| *A61B 5/055* | (2006.01) |
| *G01R 33/56* | (2006.01) |
| *G01R 33/48* | (2006.01) |

(52) U.S. Cl.
CPC .......... *G01R 33/5611* (2013.01); *A61B 5/055* (2013.01); *G01R 33/4824* (2013.01); *G01R 33/5608* (2013.01)

(58) Field of Classification Search
CPC ............ G01R 33/4824; G01R 33/5608; G01R 33/5611; A61B 5/055
See application file for complete search history.

(56) References Cited

U.S. PATENT DOCUMENTS

| | | |
|---|---|---|
| 6,289,232 B1 | 9/2001 | Jakob et al. |
| 6,841,998 B1 | 1/2005 | Griswold |
| 7,202,666 B2 | 4/2007 | Wang et al. |
| 7,205,765 B2 | 4/2007 | Machida et al. |
| 7,495,437 B2 | 2/2009 | Griswold et al. |
| 7,511,495 B2 | 3/2009 | Kholmovski et al. |
| 7,652,474 B2 | 1/2010 | Griswold et al. |

(Continued)

FOREIGN PATENT DOCUMENTS

WO    2018187005 A1    10/2018

*Primary Examiner* — Gregory H Curran
(74) *Attorney, Agent, or Firm* — Dinsmore & Shohl LLP

(57) ABSTRACT

A method for reconstructing a full k-space dataset using parallel magnetic resonance (MR) imaging technique is provided. The method includes acquiring, by a plurality of receiver coils, a set of first under-sampled k-space data, receiving a set of second partial or fully-sampled k-space data, respectively performing k-space interpolation of the set of the first under-sampled k-space data respectively acquired by each of the plurality of receiver coils, recovering respectively missing k-space lines of each of the set of first under-sampled k-space data using corresponding second partial or fully-sampled k-space data and corresponding first under-sampled k-space data, forming a plurality of full k-space datasets by respectively combining each of the set of first under-sampled k-space data and corresponding recovered missing k-space lines for each of the plurality of receiver coils, obtaining a plurality of fully-sampled images from the plurality of full k-space datasets, and combining images into a final image.

20 Claims, 13 Drawing Sheets

(56) References Cited

U.S. PATENT DOCUMENTS

| | | | |
|---|---|---|---|
| 7,688,068 B2 | 3/2010 | Beatty | |
| 7,768,264 B1 | 8/2010 | Brau et al. | |
| 7,840,045 B2 | 11/2010 | Guo et al. | |
| 7,940,044 B2 | 5/2011 | Griswold et al. | |
| 8,207,734 B2 | 6/2012 | Takahashi et al. | |
| 8,219,176 B2 | 7/2012 | Doyle | |
| 8,400,152 B2 | 3/2013 | Lin | |
| 8,692,549 B2 | 4/2014 | Grady et al. | |
| 8,717,024 B2 | 5/2014 | King et al. | |
| 9,018,952 B2 | 4/2015 | Riederer | |
| 9,097,780 B2 | 8/2015 | Liu et al. | |
| 9,153,060 B2 | 10/2015 | Ding et al. | |
| 9,229,082 B2 * | 1/2016 | Guo | G01R 33/5611 |
| 9,310,452 B2 | 4/2016 | Ahmad et al. | |
| 9,317,917 B2 | 4/2016 | Stemmer | |
| 9,390,521 B2 | 7/2016 | Lin et al. | |
| 9,588,207 B2 | 3/2017 | Weller et al. | |
| 9,983,283 B2 | 5/2018 | Daniels | |
| 2003/0076099 A1 | 4/2003 | Hajnal et al. | |
| 2015/0346305 A1 * | 12/2015 | King | G01R 33/5611 324/309 |
| 2016/0154079 A1 * | 6/2016 | Jellus | G01R 33/5611 324/309 |
| 2018/0095143 A1 | 4/2018 | Zeller | |
| 2019/0086501 A1 | 3/2019 | Bydder et al. | |

\* cited by examiner

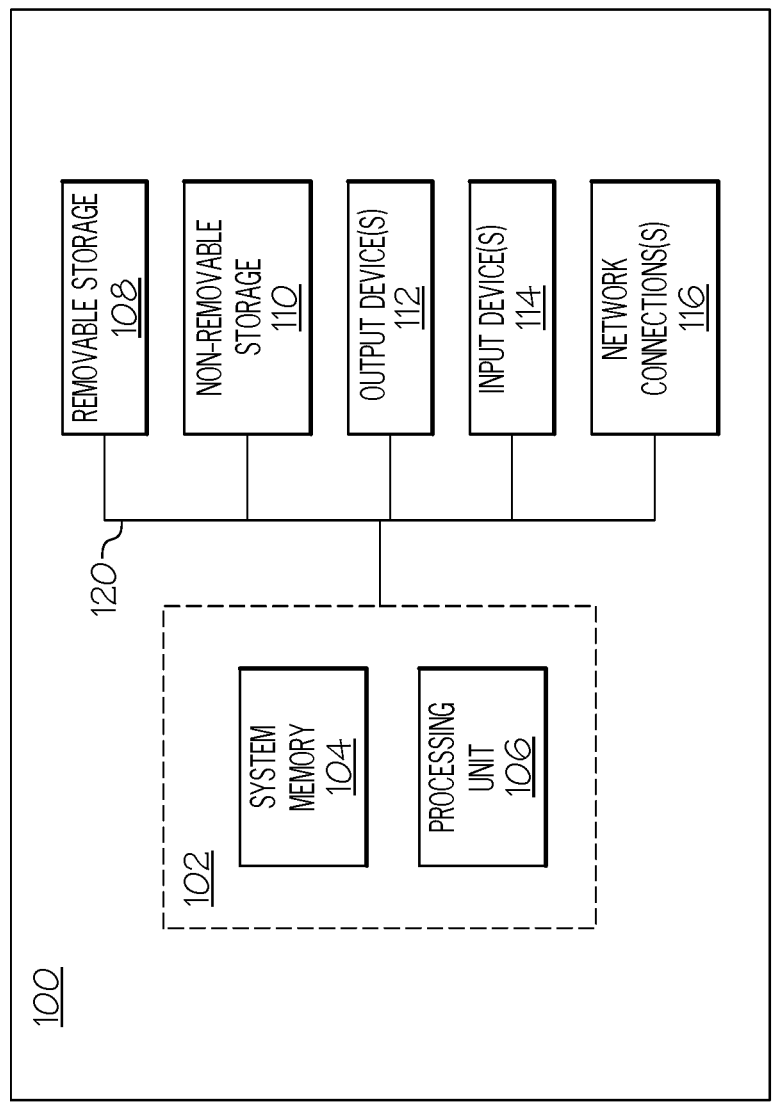

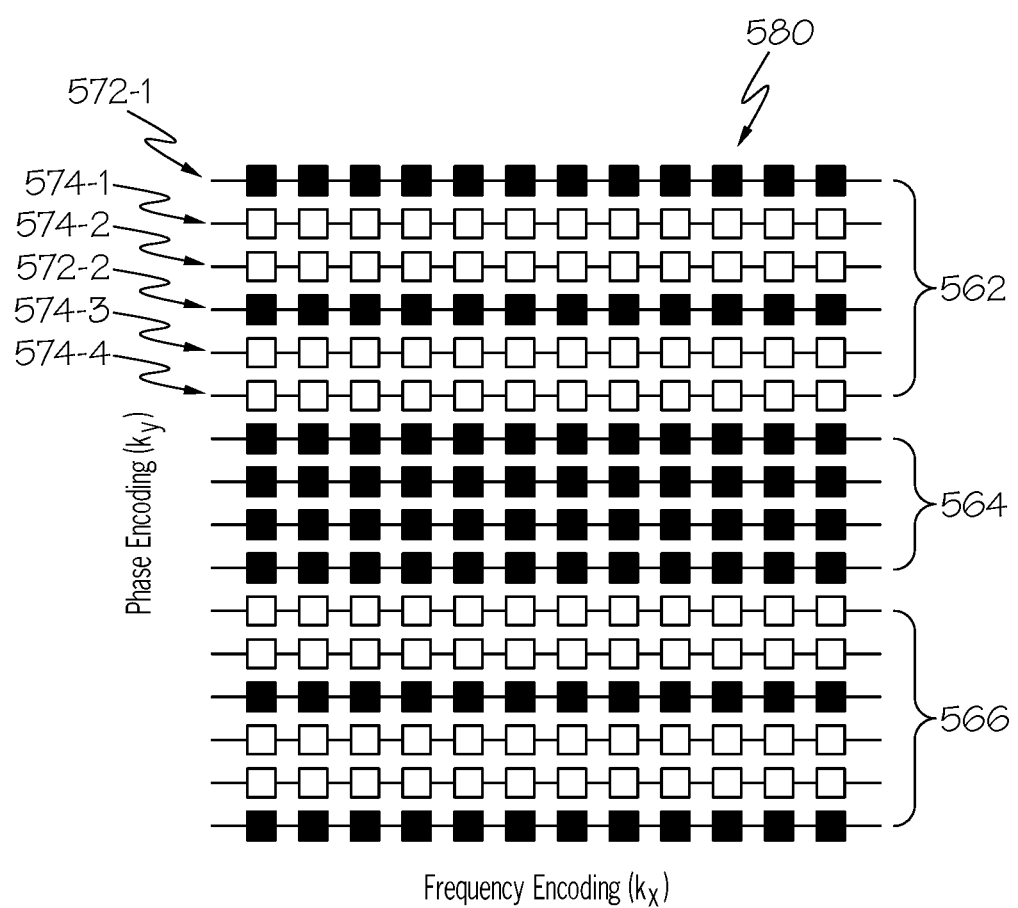
FIG. 5A1

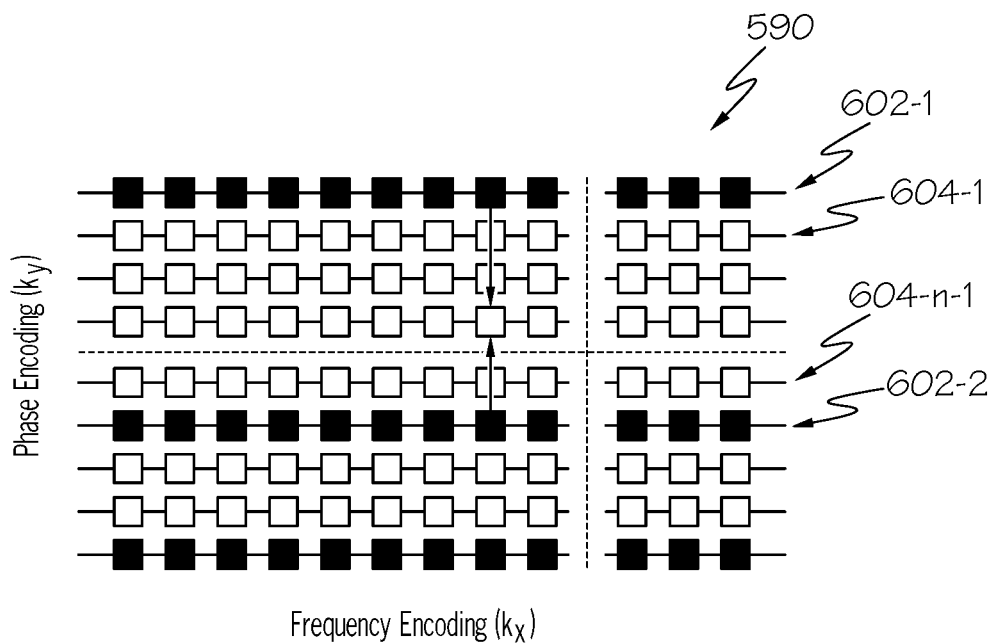
FIG. 5A2
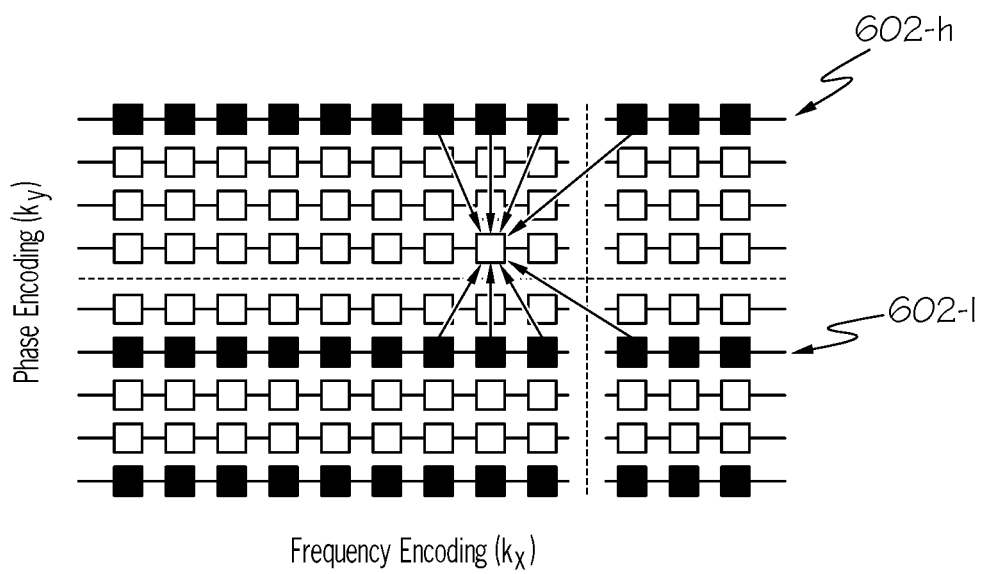
FIG. 5A3

SYSTEM AND METHOD FOR PARALLEL MAGNETIC RESONANCE IMAGING

CROSS-REFERENCE TO RELATED APPLICATION

This application claims benefit of U.S. Provisional Application No. 62/829,676 filed on Apr. 5, 2019, the entire contents of which are herein incorporated by references.

BACKGROUND

1. Field of the Invention

The present invention relates to methods and systems for parallel magnetic resonance imaging reconstruction.

2. Description of the Related Art

Magnetic Resonance Imaging (MRI) is one of the most important modern medical imaging modalities. It has far less risk of side effects than most other imaging modalities such as radioscopy with x-rays or computed tomography because patients and medical personnel are not subjected to ionizing radiation exposure in the procedure. The use of MRI has grown very fast. Every year, more than 30 million MRI scans are performed in the United States, and more than 60 million MRI scans are performed worldwide. Doctors often recommend MRI for the diagnosis of various diseases, such as tumors, strokes, heart problems, and spine diseases. A high-quality scan is important for maximizing diagnostic sensitivity and accuracy. Generally, high quality images are characterized by high signal to noise ratio (SNR), high contrast between normal and pathological tissues, low levels of artifacts, and appropriate spatial-temporal resolution In order to obtain a detectable MR signal, the object/subject examined is positioned in a homogeneous static magnetic field so that the object's nuclear spins generate net magnetization oriented along the static magnetic field. The net magnetization is rotated away from the static magnetic field using a radio frequency (RF) excitation field with the same frequency as the Larmor frequency of the nucleus. The angle of rotation is determined by the field strength of the RF excitation pulse and its duration. In the end of the RF excitation pulse, the nuclei, in relaxing to their normal spin conditions, generate a decaying signal (the "MR signal") at the same radio frequency as the RF excitation. The MR signal is picked up by a receiver coil, amplified and processed. The acquired measurements, which are collected in the spatial frequency domain, are digitized and stored as complex numerical values in a k-space matrix. An associated MR image can be reconstructed from the k-space data, for example, by an inverse 2D or 3D fast Fourier transformation (FFT) of the k-space data.

Imaging speed is one of the most important considerations in clinical MRI. Parallel MR imaging is now a clinically standard set of techniques using multiple receiver coils for partial spatial encoding to reduce k-space sampling along phase-encoding directions. That is, the undersampled in k-space according to the Nyquist theorem, is acquired with the use of multiple receiver coils. Each receiver coil or coil element is spatially-independent and includes some spatial information that can be used for a spatial encoding. The parallel imaging technique can be used to reduce scan time or increase temporal resolution given a sequence and increase the spatial resolution given a specific measurement time. The goal of parallel imaging reconstruction is reconstruct the missing k-space data with suitable algorithms and models. Generally, the missing k-space data are generated from the measured k-space data on the basis of spatial receiver sensitivity for the receiver coils, and the fully sampled sub-region k-space data. So far, parallel imaging has not only been shown to be successful in reducing scan time, but also reducing image blurring and geometric distortions. Moreover, parallel imaging can be used to improve spatial or temporal resolution as well as provide increased volumetric coverage. However, there exist two major challenges for parallel MR imaging technique. First, the SNR decreases with the square root of the acceleration factor r, and directly with the geometry factor. Second, some artifacts are caused by different reconstruction algorithms. For example, inaccurate coil sensitivities will lead to image artifacts in coil sensitivities (SENSE) reconstruction and degrade image quality.

There are two category approaches to reconstructing the image in parallel imaging methods: image-based and k-space based methods. Image-based methods reconstruct images from each coil element with reduced FOV and then combining the images using knowledge of individual coil sensitivities. A number of parallel image reconstruction techniques in image domain are disclosed in the following references:

U.S. Patent Application Publication No. 2003/0076099A1 to Joseph V. Hajnal et al. discloses a method and apparatus to reconstruct image acquired by at least two receive coils with reduced k-space data using the estimated coil sensitivities.

U.S. Pat. No. 7,205,765B2 to Yoshio Machida et al. discloses a method and a system to reconstruct the image acquired by parallel imaging technique by an unfolding field of view (FOV) that is larger than the image FOV.

U.S. Pat. No. 7,202,666B2 to Jian Min Wang and Bida Zhang discloses a method and a system to reconstruct the image acquired by parallel imaging technique by k-space sensitivity encoding. The method includes calculating the sensitivity distribution of MR reception coils each having an associated coil channel; based on the calculated sensitivity of the coils, merging the received MR signals from the respective coil channels to obtain merged data; using the merged data to perform data fitting in k-space, and finding optimal fitting parameters; and reconstructing an image using the fitting parameters to remove artifacts in the image produced from the k-space data.

U.S. Pat. No. 7,940,044B2 to Mark Griswold et al. discloses a method and apparatus to reconstruct an image acquired with parallel imaging technique. The method includes estimating individual sensitivities of receiver coils; and selecting a phase-encoding direction for a pMRI session based on the individual sensitivities. The major difference between SENSE and this method is to add the steps for selecting phase-encoding direction.

U.S. Pat. No. 8,207,734B2 to Tetsuhiko Takahashi et al. discloses a method and a system to reconstruct an image acquired by parallel image technique in non-cartesian magnetic resonance imaging using coil sensitivity distribution.

U.S. Pat. No. 8,219,176B2 to Mark Doyle discloses a method for parallel imaging using a single coil with at least two channels.

U.S. Pat. No. 9,018,952B2 to Stephen J Riederer discloses a method and a system to reconstruct the image acquired by parallel imaging technique. In the method, calibration data is acquired with image data for a selected number of time frames in a time-series. Each time frame of k-space data that contains calibration data samples a different portion of the total calibration sampling pattern, thereby mitigating undesirable reductions in the acceleration factor. The method improves the temporal scan requirements of previous SENSE-like acquisitions.

All image domain methods mentioned above require additional coil sensitivity information to reconstruct the images with under-sampled k-space data. The quality of reconstructed images strongly depend on the accurate estimation of receiver coil sensitivities. So far, the in vivo estimation of receiver coil sensitivity is very difficult, particularly for complex receiver coil sensitivity. Two major challenges for estimating the coil sensitivity of a receiver coil are (1) that the coil sensitivity should be determined in vivo because the various characteristic of subject being images (such as conductivity and permeability) strongly influence the accuracy of coil sensitivity; and (2) other various factors (such as proton density of nuclear spins and transmit field) always entangle with the receiver sensitivity to contribute to the complex MRI or MRS signals. It is very difficult to separate these factors to extract the complex coil sensitivity accurately.

Parallel image reconstruction also can be conducted in k-space domain (or frequency domain), for example Simultaneous Acquisition of Spatial Harmonics (SMASH) and GeneRalized Autocalibrating Partially Parallel Acquisition (GRAPPA). These methods explicitly calculate the missing k-space lines before Fourier transformation of the raw data is performed. SMASH method assumes that the missing phase-encoding k-space data in under-sampled k-space can be generated by a linear combination of these estimated coil sensitivities. GRAPPA method generates the missing k-space data using acquired k-space data in the k-space locations closest to the missing k-space position in the PE directions with the correlation of multiple receive coils. That is, GRAPPA reconstructs the missing k-space in each receiver coil by applying convolution kernels that are estimated from fully-sampled k-space auto-calibration signal lines using linear regression. Numerous techniques for parallel image reconstruction in k-space domain or frequency domain are disclosed in the following references:

U.S. Pat. No. 6,289,232B1 to Peter M. Jakob et al. discloses a method and apparatus to reconstruct image based on filled additional lines of the matrix from each measurement using weights or coefficients estimated by auto-calibration signals.

U.S. Pat. No. 6,841,998B1 to Mark Griswold discloses a method and apparatus to reconstruct image by forming a complete k-space dataset in k-space from the reduced k-space dataset from that receive coil and the reduced k-space dataset from at least one other of said receive coils. This reconstruction method applies correlation information between receive coils to estimate the missing k-space data.

U.S. Pat. No. 7,495,437B2 to Mark Griswold et al. discloses a method and apparatus to reconstruct image in k-space domain. The missing k-space data is calculated using the correlations among multiple receive coils.

U.S. Pat. No. 7,511,495B2 to Evgueni G. Kholmovski et al. discloses a method and apparatus to reconstruct parallel image acquisition. The missing k-space data are determined by linear combination of the acquired MRI data within neighborhoods in k-space domain that depend on imaging geometry, coil sensitivity characteristics, and the under-sampling factor of the acquired MRI data.

U.S. Pat. No. 7,840,045B2 to Junyu Guo et al. discloses a method and apparatus to reconstruct image in k-space domain. The method includes acquiring a full k-space dataset for a first frame and a partial k-space dataset for other frames; calculating reconstruction coefficients from the first dataset (the complete k-space data) from multiple receiver coils to estimate the missing k-space lines in the corresponding k-space segments of the other frame.

U.S. Pat. No. 7,652,474B2 to Mark A. Griswold et al. discloses a method and a system to reconstruct the image acquired by parallel imaging technique. The method includes controlling a parallel magnetic resonance imaging apparatus to acquire a first MR signal from a partial k-space data that includes acquiring one or more fully sampled auto-calibrating signal lines from the first partial k-space data using a phased array of receiving coils; synthesizing a second MR signal associated with the second point based, at least in part, on the first MR signal and the conjugate symmetry relation; and reconstructing an MR image based, at least in part, on both the first MR signal and the second MR signal. That is, the missing k-space data is obtained by a conjugate symmetry of the first partial k-space data.

U.S. Pat. No. 7,688,068B2 to Philip James Beatty discloses a method and a system to reconstruct the image acquired by parallel imaging technique with compressed sensing. The method includes synthesizing un-acquired MR data by way of a parallel imaging technique for a portion of k-space location; and combining the acquired under-sampled MR data and the synthesized portion of un-acquired MR data to generate a resultant MR data set.

U.S. Pat. No. 7,768,264B1 to Anja C. S. Brau and Philip James Beatty discloses a method and a system to reconstruct the image acquired by parallel imaging technique. This method includes calculating reconstruction weights; synthesizing un-acquired data directly from acquired data in k-space using an algorithm; and generating an image of the field of view from the linear combination coefficient weights and the k-space data acquired in the accelerated scan. The missing k-space data is generated using correlation values from a set of calibration data obtained by multiple receiver coils.

U.S. Pat. No. 8,692,549B2 to Leo Grady and Jonathan R. Polimeni discloses a method and a system to reconstruct the image acquired by parallel imaging technique and the compressed sensing in an iterative approach or joint energy optimization approach. The missing k-space data is generated using the correlations between multiple receive coils.

U.S. Pat. No. 8,717,024B2 to Kevin F. King and Dan Xu discloses a method and a system to reconstruct the image acquired by parallel imaging technique. The missing k-space data for each receive coil is synthesized by the portion of the calibration data and the reconstruction weights calculated from a small amount of fully sampled calibration data.

U.S. Pat. No. 9,097,780B2 to Jun Liu et al. discloses a method and a system to reconstruct the image acquired by parallel imaging technique. The missing k-space data for each receive coil is obtained by the fitting process. The fitting process includes determining a linear combination of the k-space lines providing a first optimal approximation of the one or more calibration lines; determining a plurality of the coefficient values associated with the linear combination; using the coefficient values to determine a plurality of missing k-space lines from the incomplete k-space data set; repeating the previous process to create complete k-space data.

U.S. Pat. No. 9,153,060B2 to Yu Ding and Orlando Simonetti discloses a method and a system of tile-all-frame to GRAPPA reconstruction of dynamic parallel images. The method uses at least two sets of ACS lines to estimate the k-space convolution kernel and thereby improve the SNR of the images reconstructed by GRAPPA.

Conventional solutions use linear constraints with iterative solvers to improve the performance of GRAPPA reconstruction. However, these solutions is not a closed-form solution. There are some ubiquitous difficulties: in defining an appropriate stopping criterion, convergence may not be guaranteed, and time-consuming. In order to overcome these difficulties, U.S. Pat. No. 9,310,452B2 to Rizwan Ahmad et al. discloses a method and a system to reconstruct the image acquired by parallel imaging technique using self-constraint condition. The method introduces a set of linear equations determined in accordance with correlations within missing k-space data as a self-constraint condition and refines the missing k-space data.

U.S. Pat. No. 9,390,521B2 to Wei Lin et al. discloses a method and a system to reconstruct the image acquired by non-Cartesian parallel imaging technique. The missing k-space data is obtained by a GRAPPA operator for wider radial bands.

U.S. Pat. No. 9,317,917B2 to Alto Stemmer discloses a method and apparatus for reconstructing magnetic resonance raw data. The missing raw data in central k-space region is estimated using raw data acquired with the respective magnetic resonance coil, and without using raw data acquired with other coils. The missing raw data in a peripheral region of k-space is estimated using raw data acquired with the respective magnetic resonance coil in central k-space region and raw data acquired with other coils.

U.S. Pat. No. 8,400,152B2 to Fa-Hsuan Lin discloses a method for parallel magnetic resonance imaging. Individual coil images are reconstructed from under-sampled scan data that is acquired with coil array having multiple coil channels. Missing k-space lines in the under-sampled scan data are synthesized by interpolating k-space lines in the acquired scan data using the reconstruction coefficients that are determined by autocalibration scan (ACS) data.

U.S. Pat. No. 9,588,207B2 to Daniel Weller et al. discloses a method and a system to reconstruct the image acquired by parallel imaging technique. This method includes deriving a first set of weights for generating a calibration data set comprising a subset of k-space data of composite image data representing the multiple image data sets; deriving a second set of weights using the calibration data set and the generated first MR image data set; uses the second set of weights in generating a second MR image data set representing a single image having a reduced set of data components relative to the first composite MR image data set. The missing k-space locations in each receiver coil is obtained using the combination of fully sampled k-space as a post-processing step.

U.S. Patent Application Publication No. 2018/0095143A1 to Mario Zeller discloses an operation process of parallel imaging reconstruction. The process includes under-sampled k-space data, fully sampled calibration k-space data, and the missing k-space data generated from under-sampled k-space data and fully sampled calibration k-space data. The known image process is disclosed. The disclosure fails to teach how to generate the missing k-space data from under-sampled k-space data and fully sampled calibration k-space data.

International Patent Application Publication No. WO/2018/187005A1 to Mehmet Akcakaya and Steen Moeller discloses a method for reconstructing images from under-sampled k-space data using a machine learning approach to learn non-linear mapping functions from acquired k-space lines to generate unacquired target points across multiple coils. This method estimates a missing k-space lines from acquired k-space data. In general, a machine learning algorithm is trained on calibration data, and enables a non-linear estimation of missing k-space lines.

U.S. Pat. No. 9,983,283B2 to Wayne R Dannels discloses a systems and methods to effect accelerated MR image reconstruction for under-sampled data acquisitions with radial strip acquisitions of k-space. The optimal under-sampled areas of k-space data is acquired by an accelerated scan such that image reconstruction may be performed with reduced artifacts.

U.S. Patent Application Publication No. 2019/0086501A1 to Mark Bydder et al. discloses a method and magnetic resonance (MR) apparatus for under-sampled MR parallel image reconstruction. A structured matrix completion algorithm is used to reconstruct images with fewer motion-induced errors.

Parallel imaging techniques use uncorrelated spatial sensitivity of each array coils for accelerated image acquisition. Increasing the number of coils in a coil array is a straightforward approach to increase the image SNR by providing more versatile sensitivity distributions. The magnitude of coupling between receiver coil array can significantly amplify noise correlations and degrade measured SNR. Since the anatomical structure can vary significantly between applications, minimizing their mutual coupling in practices can be very challenging. For image acquisition, various methods, such as overlapping adjacent receiver coils and inserting inductors and/or capacitors between adjacent receiver coils, have been proposed to minimize the mutual coupling. However, for parallel imaging reconstruction, existing k-space domain methods mentioned above employs correlation of k-space data between or among receive coils to generate the missing k-space that are under-sampled in parallel imaging technique basing on the calculation or interpolation of a linear combination of all measured data points. As a result, the introduced correlation may reduce spatial independence of each coil element, introduce the reconstructed artifacts and degrade the performance of parallel imaging, particularly for high accelerated factors.

SUMMARY

An object of the present invention is to provide a method and a system for parallel imaging reconstruction techniques with a slight increase in SNR and slight under-sampling artifacts in the reconstructed image.

In one embodiment, a method for reconstructing a full k-space dataset using parallel magnetic resonance (MR) imaging technique is provided. The method includes acquiring, by a plurality of receiver coils, a set of first under-sampled k-space data related to a target area of an object respectively corresponding to the plurality of receiver coils, receiving a set of second partial or fully-sampled k-space data related to the target area respectively corresponding to the set of first under-sampled k-space data, respectively performing k-space interpolation of the set of the first under-sampled k-space data respectively acquired by each of the plurality of receiver coils, recovering respectively missing k-space lines of each of the set of first under-sampled k-space data using corresponding second partial or fully-sampled k-space data and corresponding first under-sampled k-space data, forming a plurality of full k-space datasets related to the target area by respectively combining each of the set of first under-sampled k-space data and corresponding recovered missing k-space lines for each of the plurality of receiver coils, obtaining a plurality of fully-sampled images from the plurality of full k-space datasets corresponding to the plurality of receiver coils, and combining images of each individual coils into a final image.

In another embodiment, a magnetic resonance imaging (MRI) method for reconstructing images acquired with both parallel imaging and partial Fourier acquisition technique using a plurality of receiver coils is provided. The method includes acquiring a set of first partial under-sampled k-space data related to a target area of an object with parallel imaging and partial Fourier acquisition using the plurality of receiver coils, respectively performing parallel imaging reconstruction by k-space interpolation of the set of first partial under-sampled k-space data respectively acquired by each of the plurality of receiver coils, recovering respectively missing k-space lines of the set of first partial under-sampled k-space data, respectively combining each of the set of first partial under-sampled k-space data and corresponding missing k-space lines to generate a set of second partial under-sampled k-space data for each of the plurality of receiver coils, respectively forming a plurality of full k-space datasets by implementing partial Fourier reconstruction on the set of second partial under-sampled k-space data, respectively reconstructing a plurality of images from the plurality of full k-space datasets, and combining the plurality of images into a final image.

In yet another embodiment, a magnetic resonance imaging (MRI) system for parallel imaging reconstruction is provided. The system includes a magnetic field generating unit configured to apply a plurality of RF pulses to a target area of an object, a plurality of receiver coils configured to receive MR signals from the target area, a processing unit, a system memory, and machine readable instructions stored in the system memory that, when executed by the processing unit, cause the processing unit to: acquire a set of first under-sampled k-space data related to a target area of an object respectively corresponding to the plurality of receiver coils, receive a set of second partial or fully-sampled k-space data related to the target area respectively corresponding to the set of first under-sampled k-space data, perform k-space interpolation of the set of the first under-sampled k-space data respectively acquired by each of the plurality of receiver coils, recover respectively missing k-space lines of each of the set of first under-sampled k-space data using corresponding second partial or fully-sampled k-space data and corresponding first under-sampled k-space data, form a plurality of full k-space datasets related to the target area by respectively combining each of the set of first under-sampled k-space data and corresponding recovered missing k-space lines for each of the plurality of receiver coils, obtain a plurality of fully-sampled images from the plurality of full k-space datasets corresponding to the plurality of receiver coils, and combine images of each individual coils into a final image.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIG. 1A is an example computing device;

FIG. 5A1 depicts an example of acquired k-space data by oversampling k-space data for a receiver coil according to one example in the present disclosure.

FIG. 5A2 depicts an example of a phase of missing k-space data to be interpolated using k-space scaling method according to one example in the present disclosure.

FIG. 5A3 depicts an example a magnitude of missing k-space data to be interpolated using k-space scaling method according to one example in the present disclosure.

DETAILED DESCRIPTION

Definition

Figure 1:
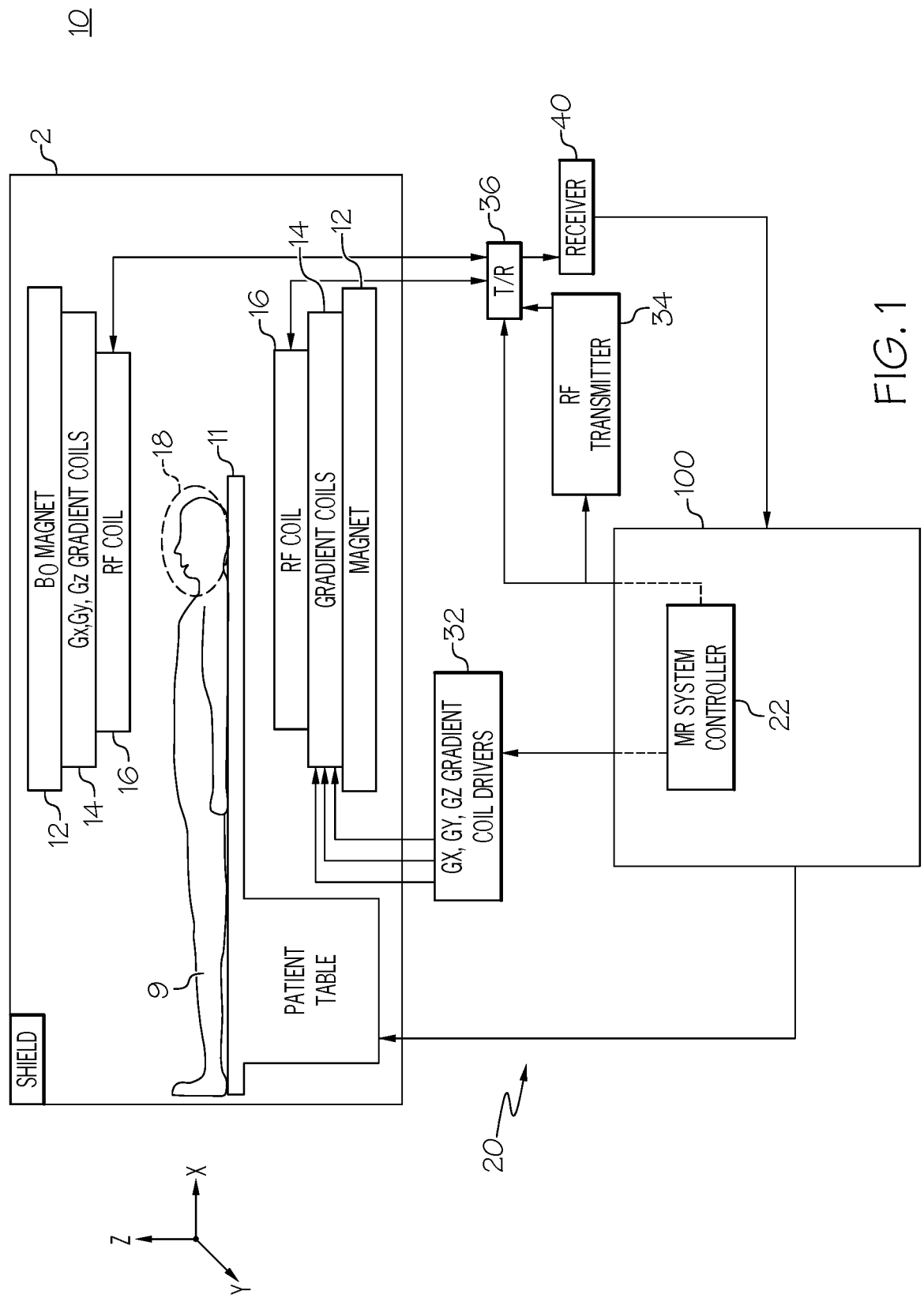
FIG. 1 is a diagram illustrating an example MRI system.

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. This disclosure contemplates that the images obtained using the techniques described herein can be directly employed in at least one of diagnosing diseases, monitoring prognosis and therapeutic responses, conducting treatment plans, and improving quantification of MRI. Additionally, the techniques described herein are optionally applicable to a group of individuals in a similar pathophysiological situation.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation.

The term "comprising" or "containing" or "including" and variations thereof as used herein indicate that at least the named compound, element, particle, or method step is present in the composition or article or method, but does not exclude the presence of other compounds, materials, particles, method steps, even if the other such compounds, material, particles, method steps have the same function as what is named The term "parallel imaging" or "partial parallel imaging" and variations thereof as used herein indicate that imaging technique is used to accelerate data acquisition in one or more dimensions by exploiting the spatial dependence of phased array coil sensitivities. Parallel imaging has an advantage not only in reducing scan time, but also in reducing image blurring and geometric distortions. Moreover, parallel imaging can be used to improve spatial or temporal resolution as well as increased volumetric coverage.

The term "k-space" and variations (such as frequency domain or raw data) thereof as used herein indicate the data space in which MRI raw data is acquired. The k-space represents the spatial frequency information in two or three dimensions of an object. The k-space is defined as a space covered by the phase and frequency encoding data. In contrast to this, the Fourier-transformed counterpart of the k-space is defined as an image space or image domain. The relationship between k-space data and image data is the Fourier transformation. Each data point in k-space represents a different superposition of the tissue signals. Every point in the raw data matrix contains part of the information for the complete image. A point in the raw data matrix does not correspond to a point in the image matrix. The high spatial frequency components provide information about the borders and contours of the image, the detail of the structures. The low spatial frequency components provide information on the general contrast of the image.

The term "k-space trajectory" and variations thereof as used herein indicate the path traced in k-space domain during MRI data collection. The k-space trajectory is used to illustrate the acquisition strategy. It has great influences on artifacts and the image reconstruction.

The term "k-space interpolation" and variations thereof as used herein indicate a process that the resolution of k-space data is increased to overcome the image artifacts, particularly for a fold-over artifact caused by under-sampled k-space in parallel imaging. For example, zero-filling is the most popular method of k-space interpolation to expand the image matrix size. Zero-filling does not add any information to the input raw data, but it can reduce partial volume artifacts and improve the sharpness of image.

The term "reconstruction" and variations thereof as used herein indicate a mathematical process that generates MRI images from incomplete raw data acquired at many different conditions to improve image quality and reduce the artefacts.

The term "the normalized root-mean-square error (NRMSE)" and variations thereof as used herein is defined as:

$$RMSE = \frac{\sqrt{\Sigma(I_{rec} - I_{ref})^2}}{\Sigma I_{ref}} \quad \text{(Equation 1)}$$

where $I_{ref}$ is the reference image reconstructed from full k-space data and $I_{rec}$ is the image reconstructed from the corresponding partial k-space data.

The term "object" or "subject" or "patient" and variations thereof as used herein may be a human or an animal or a phantom.

MRI System Overview

FIG. 1 depicts an MRI system 10, according to one or more embodiments described and shown herewith. In embodiments, the MRI system 10 shown in FIG. 1 includes a patient table 11, a static magnetic field generating unit 12, a gradient magnetic field generating unit 14 for generating respective magnetic fields in proximity to a target area 18 of an object 9, a transmitting and receiving unit 16, and a computing device 100. The patient table 11, the static magnetic field generating unit 12, the gradient magnetic field generating unit 14, and the transmitting and receiving unit 16 are placed within MRI RF shielding area 2 where noise of radio frequency is prevented from entering.

The static magnetic field generating unit 12 includes a main magnet configured to generate a strong static magnetic field in proximity to the target area 18 of the object 9. The static magnetic field generating unit 12 may be arranged to surround the target area 18 of the object 9. For example, the static magnetic field generating unit 12 may be a cylindrical-shaped unit. The gradient magnetic field generating unit 14 includes gradient magnetic field coils for generating gradient magnetic fields in an x-axis direction, a y-axis direction, and a z-axis direction, which are orthogonal to each other. The gradient magnetic field generating unit 14 may be arranged to surround the target area 18 of the object 9. For example, the gradient magnetic field generating unit 14 may be a cylindrical-shaped unit.

In embodiments, the transmitting and receiving unit 16 may include a transmission coil and a receiving coil. The transmission coil irradiates RF pulses to the object 9 and the receiving coil receives MR signals generated by the object 9. In some embodiments, the transmitting and receiving unit 16 may include a transceiver coil having the functions of both the transmission coil and the receiving coil. The receiving coil may be composed of, for example, a so-called array coil in which, for example, a plurality of coil elements are disposed to detect the MR signals generated by the object 9. An RF transmitter 34 may control the transmission coil of the transmitting and receiving unit 16 to irradiate RF pulses. A receiver 40 may receive MR signals generated by the object 9 from the receiving coil of the transmission and receiving unit 16. The RF transmitter 34 and the receiver 40 may communicate with the transmitting and receiving unit 16 through a transmitter/receiver interface 36.

In embodiments, the MRI system 10 includes the computing device 100. The computing device 100 includes a MRI system controller 22. The MRI system controller 22 may control the operations of the gradient coil drivers 32 that activate the gradient coils of the gradient magnetic field generating unit 14. The MRI system controller 22 may also control the operations of the RF transmitter 34 that activates the RF coil of the static magnetic field generating unit 12. The computing device 100 may receive MR signals from the receiving coil of the transmission and receiving unit 16 and reconstruct an MRI image based on the received MR signals.

The details of the computing device 100 will be further described with reference to FIG. 1A below.

In embodiment, the computing device 100 may be operably coupled to other components of the MRI system 10, for example, using by any medium that facilitates data exchange between the components of the MRI system 10 and the computing device 100 including, but not limited to, wired, wireless and optical links. For example, the computing device 100 may convert the MR signals received from the transmitting and receiving unit 16 into k-space data. The computing device 100 may generate MR image data from the k-space data with image reconstruction processing. In some embodiments, the techniques for improving image quality with optimal variable flip angles may optionally be implemented using the MRI system 10.

Example Computing Device

FIG. 1A depicts a computing device 100 according to one or more embodiments shown and described herein. It should be appreciated that the logical operations described herein with respect to the various figures may be implemented (1) as a sequence of computer implemented acts or program modules (i.e., software) running on a computing device (e.g., the computing device described in FIG. 1A), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

It should be understood that the computing device 100 is only one example of a suitable computing environment upon which embodiments of the invention may be implemented.

Optionally, the computing device 100 may be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In embodiments, the computing device 100 includes a controller 102 that includes one or more processing units 106 and one or more system memory modules 104. The controller 102 may be the same controller as the MRI system controller 22 in FIG. 1. In other embodiments, the controller 102 may be a separate controller from the MRI system controller 22 in FIG. 1. Depending on the exact configuration and type of computing device, the one or more memory modules 104 may be volatile (such as random access memory (RAM)), non-volatile (such as read-only memory (ROM), flash memory, etc.), or some combination of the two. The one or more processing units 106 may be a standard programmable processor that performs arithmetic and logic operations necessary for operation of the computing device 100.

In embodiments, the computing device 100 includes communication path 120 that provides signal interconnectivity between various components of the computing device 100. Accordingly, the communication path 120 may communicatively couple any number of processing units 106 with one another, and allow the components coupled to the communication path 120 to operate in a distributed computing environment. Specifically, each of the components may operate as a node that may send and/or receive data. As used herein, the term "communicatively coupled" means that coupled components are capable of exchanging data signals with one another such as, for example, electrical signals via conductive medium, electromagnetic signals via air, optical signals via optical waveguides, and the like.

Accordingly, the communication path 120 may be formed from any medium that is capable of transmitting a signal such as, for example, conductive wires, conductive traces, optical waveguides, or the like. In some embodiments, the communication path 120 may facilitate the transmission of wireless signals, such as Wi-Fi, Bluetooth, Near Field Communication (NFC) and the like. Moreover, the communication path 120 may be formed from a combination of mediums capable of transmitting signals. In one embodiment, the communication path 120 comprises a combination of conductive traces, conductive wires, connectors, and buses that cooperate to permit the transmission of electrical data signals to components such as processors, memories, sensors, input devices, output devices, and communication devices. Accordingly, the communication path 120 may comprise a vehicle bus, such as for example a LIN bus, a CAN bus, a VAN bus, and the like. Additionally, it is noted that the term "signal" means a waveform (e.g., electrical, optical, magnetic, mechanical or electromagnetic), such as DC, AC, sinusoidal-wave, triangular-wave, square-wave, vibration, and the like, capable of traveling through a medium.

The one or more processing units 106 may be configured to execute program code encoded in tangible, computer-readable media. Tangible, computer-readable media refers to any media that is capable of providing data that causes the computing device 100 (i.e., a machine) to operate in a particular fashion. Various computer-readable media may be utilized to provide instructions to the one or more processing units 106 for execution. Example tangible, computer-readable media may include, but is not limited to, volatile media, non-volatile media, removable media and non-removable media implemented in any method or technology for storage of information such as computer readable instructions, data structures, program modules or other data. One or more system memory modules 104, a removable storage 108, and a non-removable storage 110 are all examples of tangible, computer storage media. Tangible, computer-readable recording media may include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In embodiments, the one or more processing units 106 may execute program code stored in the one or more system memory modules 104. For example, a bus may carry data to the one or more system memory modules 104, from which the one or more processing units 106 receive and execute instructions. The data received by the one or more system memory modules 104 may be optionally stored on the removable storage 108 or the non-removable storage 110 before or after execution by the processing unit 106.

In embodiments, the computing device 100 may include additional storage such as removable storage 108 and non-removable storage 110 including, but not limited to, magnetic or optical disks or tapes.

The computing device 100 may also have input device(s) 114 such as a keyboard, mouse, touch screen, etc. The input device may be manipulated by an operator to input signals to the MRI apparatus to set the imaging method group, the performing order, the imaging condition, and the like. The computing device 100 may also have output device(s) 112 such as a display, speakers, printer, etc. The output device 112 may output image data such as local image data, diagnosis image data using display, printer and other displayer. The additional devices may be connected to the bus in order to facilitate communication of data among the components of the computing device 100.

Computing device 100 may also contain network connection(s) 116 that allow the device to communicate with other devices. The network connection(s) 116 may be any device capable of transmitting and/or receiving data via a wireless network. Accordingly, the network connection(s) 116 may include a communication transceiver for sending and/or receiving data according to any wireless communication standard. For example, the network connection(s) 116 may include a chipset (e.g., antenna, processors, machine readable instructions, etc.) to communicate over wireless computer networks such as, for example, wireless fidelity (Wi-Fi), WiMax, Bluetooth, IrDA, Wireless USB, Z-Wave, ZigBee, or the like.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

In some embodiments, the computing device 100 may include a workflow setting unit, an imaging operation determining unit, and an image reconstruction unit. The workflow setting unit may be a program module stored in the system memory modules 104. The workflow setting unit sets a first workflow relating to the MRI examination by estimating an imaging time of each of the imaging methods in the performing order initially set by a scan plan. Further, the workflow setting unit sets a second workflow relating to the MRI examination by estimating a shortest performing order, by which an examination time necessary to sequentially perform a plurality of imaging methods constituting the imaging method group set by, the input unit is minimized. The imaging operation determining unit determines whether an imaging operation during a main imaging is implemented according to the workflow. In embodiments, the workflow setting unit and/or the imaging operation unit may be implemented using hardware, software, and or a combination thereof.

The image reconstruction unit may include an MR signal storage unit, a signal processing unit, and an image data storage unit. The MR signal storage unit (e.g., memory) stores the MR signals, which are collected by the receiver unit of the transmitting and receiving unit 16. The signal processing unit has an image reconstruction processing unit and an image processing unit. The image reconstruction processing unit generates image data from the MR signal storage unit by image reconstruction processing, for example, performed by a Fourier transformation such as 2D FFT. When the MR signals to a three-dimensional region are collected, the image reconstruction processing unit of the signal processing unit generates volume data. Subsequently, the image processing unit generates three-dimensional image data such as volume rendering image data, surface rendering image data and the like or two-dimensional image data, multi planar reconstruction image data, and the like, because predetermined image processing is performed for the volume data generated by the image reconstruction processing unit. Then, the image data described above obtained by the signal processing unit are stored to the respective storage regions of the image data storage unit.

Overview

Parallel imaging was first introduced in the late 1990s for reducing scan time using multiple receiver coils since receiver sensitivity could be used for encoding. The shortening the total scan time can improve patient compliance, which is vital for pediatric patients and patients with neurodegenerative diseases. Savings in scan time can be invested in enhancing the spatial resolution or increasing the volumetric coverage. Additionally, parallel imaging can reduce the echo train length, which decreases blurring from $T_2^*$ or $T_2$ effects and geometric distortion, particularly in echo planar imaging.

Parallel imaging techniques fall into two category approaches, depending on whether aliased pixels are separated in the image domain or missing phase encoding lines are reconstructed in k-space. Image-based methods mainly include SENSE and its variations. These methods have a primary limitation which requires accurate knowledge of the sensitivities of the component coils. The major challenge for estimating the coil sensitivity of a receiver coil accurately is the factor that other various factors (such as proton density of nuclear spins and transmit field) always entangle with the receiver sensitivity to contribute to the complex MRI or MRS signals. It is very difficult to separate these factors to extract the complex coil sensitivity accurately. Additionally, noise and motion between coil calibration and scan acquisition also influence the accuracy of estimating receive sensitivity.

In order to avoid the accurate estimation of receiver sensitivity, GRAPPA method was introduced to reconstruct parallel imaging in k-space domain in 2002. As for GRAPPA and its variation, accurate coil sensitivity is not needed before image reconstruction. These methods assume that all k-space data within a neighborhood are correlated. The missing k-space lines can be generated according to the correlation between coil elements. The GRAPPA algorithm results in uncombined single coil images, which can be combined using a magnitude reconstruction procedure. Additional calibration k-space data points are necessarily acquired in the actual measurement data for estimating or formulating the correlation within a neighborhood. The major limitation of these k-space based methods is the factor that these methods can work well for low reduction factors, but introduce residual aliasing artifacts and substantial noise amplification in the reconstructed images for high reduction factors. The assumption of existed k-space domain methods that all k-space data within a neighborhood from each coil or coil element are correlated is not consistent to the basic concept that uses spatial information for encoding from each coil or coil element in parallel imaging. If the correlation between coil elements are very strong, the coil elements should not be regarded as a multiple coil array but a single coil. This is a major and basic problem for GRAPPA and its variation method in parallel imaging, though a lot of evidences show that GRAPPA and its variation methods work very well for low reduction factors.

Parallel imaging methods, including SENSE and GRAPPA and their variations, are based on spatial information for encoding from each coil or coil element to reduce the k-space data samples and scan time. As a result, each coil or coil element is expected to be independent each other, and a number of techniques have been developed for decoupling the individual coil or coil element. However, existed k-space domain methods, such as GRAPPA and its variations assume that all k-space data from each coil or coil element are correlated. Therefore, correlation among coils are inconsistent with independent spatial encoding. In order to solve this problem, the present disclosure provides a method where the missing k-space data of a receiver coil is generated using k-space data acquired by the same receiver coil. Recovering missing k-space data of a receiver coil using the same receiver coil without referring to correlation among k-space data within a neighborhood is different from previous k-space method for parallel imaging reconstruction, such as GRAPPA.

Figure 2:
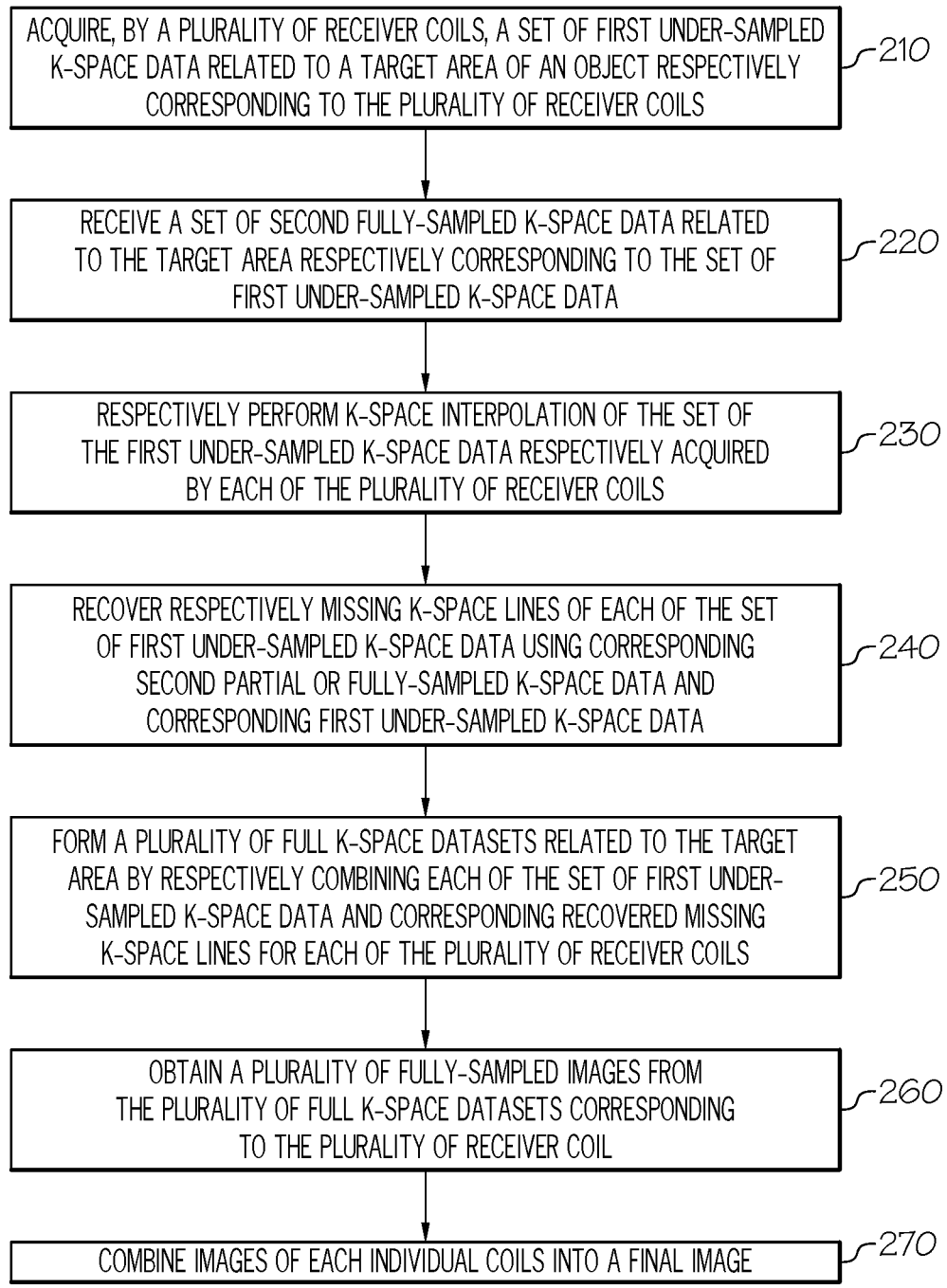
FIG. 2 is a flowchart illustrating an example operation for reconstructing a full k-space dataset of a coil element in parallel magnetic resonance (MR) imaging technique according to one example in the present disclosure.

FIG. 2 is a graph illustrating an example operation for a method for reconstructing a full k-space dataset of a coil element in parallel magnetic resonance (MR) imaging technique according to one example in the present disclosure.

Figure 3:
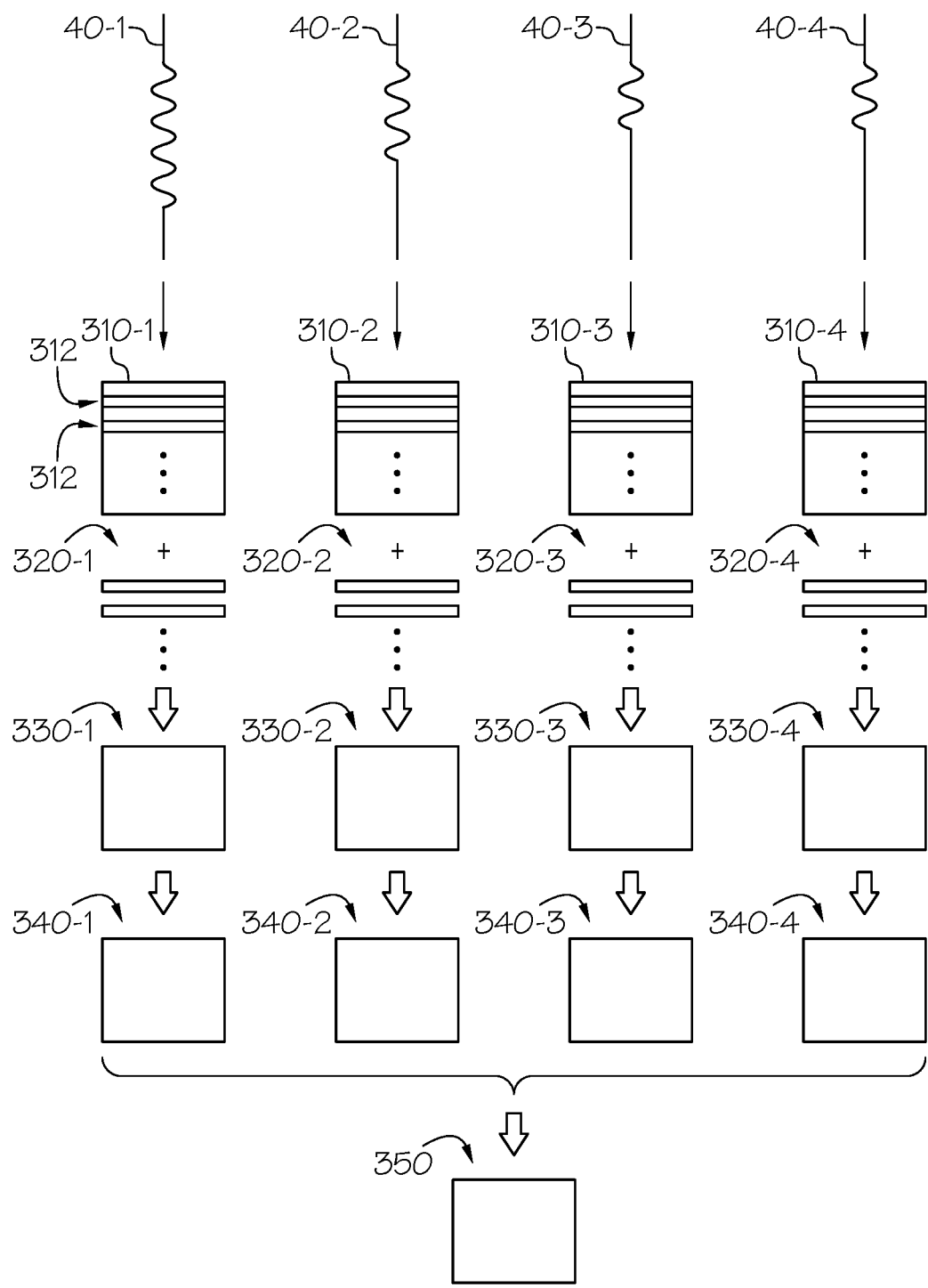
FIG. 3 is a schematic diagram for reconstructing a full k-space dataset of each receiver coil in parallel magnetic resonance (MR) imaging technique according to one example in the present disclosure.

In step 210, the computing device 100 acquires, by a plurality of receiver coils, a set of first under-sampled k-space data related to a target area of an object respectively corresponding to the plurality of receiver coils. In embodiments, as shown in FIG. 1, the computing device 100 receives MR signals from the transmitting and receiving unit 16 using parallel magnetic resonance (MR) imaging and acquires a set of first under-sampled k-space data for the target area 18 of the object 9. By referring to FIGS. 1 and 3, the receiver 40 may include a plurality of receiver coils such as receiver coils 40-1, 40-2, 40-3, 40-4. While FIG. 3 depicts four receiver coils, more than or less than four receiver coils may be used. Each of the receiver coils 40-1, 40-2, 40-3, 40-4 may acquire first under-sampled k-space data for the target area 18 of the object 9, respectively. For example, the receiver coil 40-1 acquires first under-sampled k-space data 310-1, the receiver coil 40-2 acquires first under-sampled k-space data 310-2, the receiver coil 40-3 acquires first under-sampled k-space data 310-4, the receiver coil 40-4 acquires first under-sampled k-space data 310-4. Each of the first under-sampled k-space data 310-1, 310-2, 310-3, 310-4 has missing k-space lines due to parallel MR imaging.

In embodiments, the k-space dataset may be acquired in phase-encoding directions. In some embodiments, the k-space dataset is acquired in frequency-encoding directions. In some embodiments, the k-space dataset may be acquired using a combination of partial Fourier acquisition and other under-sampling techniques, such as compressed sensing and parallel imaging acquisitions.

In embodiments, the k-space dataset may be acquired with at least one of $T_1$-weighted spin echo, $T_2$-weighted spin echo, fluid-attenuated inversion-recovery, $T_1$-weighted gradient-echo, $T_2^*$-weighted gradient echo, contrast enhanced $T_1$-weighted gradient echo, contrast enhanced $T_1$-weighted spin echo, diffusion-weighted spin echo, and their variations or combinations.

In embodiments, the k-space dataset may be acquired with imaging sequence including, but not limited to, at least one of two spatial dimensional, three spatial dimensional, or three spatial dimensional plus temporal image acquisition. In some embodiments, the imaging sequence may include at least one of a gradient echo, echo planar or spin echo sequence with or without magnetization preparation, with or without under-sampling techniques, with or without parallel imaging techniques, or with or without Cartesian k-space trajectories. The imaging sequence can include at least one of two spatial dimensional, three spatial dimensional, or three spatial dimensional plus temporal image acquisition. For example, dynamic contrast agent enhanced imaging and blood oxygen level dependent functional MRI may deal with motion at the different time frames.

In embodiments, the k-space dataset may be acquired using k-space trajectory including at least one of rectilinear, echo planar, but not limited to, radial, Cartesian, non-Cartesian, Zig-Zag, stochastic, rosette, TWIRL, WHIRL and spiral trajectories. The k-space dataset may be acquired according to a k-space sampling order including at least one of a sequential sampling order, a centric sampling order, an interleave sampling order, a reverse sampling order, a random sampling order, or a hybrid sampling order.

In embodiments, the k-space data may be acquired by a combination of partial Fourier acquisition, simultaneous multi-slice imaging techniques, and other under-sampling techniques, such as compressed sensing and parallel imaging acquisitions. In some embodiments, the method can be extended for dynamic parallel imaging acquisition at the different time frames.

In embodiments, the computing device 100 acquires a k-space dataset for a region of interest using an MR scanner. The region of interest may include at least a portion of a subject's body with or without disease. The portion of the subject's body may be at least one of an extremity, brain, spine, neck, chest, breast, joint, prostate, pelvis, or abdomen.

In step 220, the computing device 100 receives a set of second partial or fully-sampled k-space data related to the target area respectively corresponding to the set of first under-sampled k-space data. Each of the set of second partial or fully-sampled k-space data is artifacts-free subset k-space data and corresponds to the set of first under-sampled k-space data, e.g., the first under-sampled k-space data 310-1, 310-2, 310-3, 310-4. In embodiments, each of the set of second partial or fully-sampled k-space data related to the target area may be acquired by oversampling the part of corresponding first under-sampled k-space data. The oversampling the part of the first under-sampled k-space data is usually conducted in the central of the first under-sampled k-space data to generate a low resolution complete full k-space data as a reference. The low resolution complete full k-space may be an artifacts-free low resolution image.

In some embodiments, each of the set of second partial or fully-sampled k-space data related to the target area may be a fully sampled MRI k-space data acquired by corresponding receiver coil or coils. The fully sampled MRI k-space data may be artifact-free k-space data. For example, a fully-sampled fast spin-echo image $T_1$-weighted image may be used as the artifact-free k-space data for reconstructing parallel acquired $T_1$-weighted spin-echo or gradient echo images. As another example, the fully sampled MRI k-space data may be low-resolution imaging, compared to the images reconstructed from the first under-sampled k-space data. The fully sampled MRI k-space data may have a similar contrast as the first under-sampled k-space data, compared to the images reconstructed from the first under-sampled k-space data.

In some embodiments, each of the set of second partial or fully-sampled k-space data related to the target area may be obtained by implementing Fourier transform of an artifact-free image in image domain. The second partial or fully-sampled k-space data can be obtained from Fourier transform of an artifact-free image acquired with other modalities, such as CT, PET or optical image. In order to improve the image quality of reconstructed parallel imaging, the second partial or fully-sampled k-space data or artifact-free k-space data is expected to have a similar contrast as the acquired first under-sampled k-space data. For example, the image contrast acquired with computer tomographer is similar to that acquired with proton density-weighted MRI.

In step 230, the computing device 100 performs k-space interpolation of the set of the first under-sampled k-space data respectively acquired by each of the plurality of receiver coils. In embodiments, the k-space interpolation may use one of three methods: k-space scaling method, k-space super-resolution method, and iterative k-space reconstruction method.

k-space scaling method performs an extension of k-space phase with linear interpolation and k-space magnitude according to the Fourier transform of the corresponding signal intensity of the given sequence that is determined by Bloch equations. Conventional k-space interpolation, such as GRAPPA and SMASH, performs an extension of k-space data using linear relationship for parallel imaging reconstruction. Signal intensities for k-space lines may be different for most fast imaging sequences, such as, 3 dimensional (3D) magnetization-prepared rapid gradient-echo sequence and single slab 3D fast spin echo sequence with slab selective, variable excitation pulse sequence. Therefore, the linear relationship approximation is not exact and can introduce a big error in parallel imaging reconstruction, particularly for a highly accelerated parallel imaging acquisition. k-space scaling method according to the present disclosure addresses the problems of the conventional k-space interpolation.

Parallel imaging acquisition technique reduces scan time using reduced number of phase encoding steps. Generally, the difference among k-space lines along phase encoding direction are caused by constant phase encoding step, object dependent features, and sequence dependent features. For most sequences, the major difference among nearest k-space lines is caused by the effect of the constant phase encoding step on k-space phase and the effect of object dependent features on k-space magnitude. In image domain, conventional interpolation methods such as nearest neighbor, bilinear, and bicubic interpolations have been used to increase the image resolution.

In the present disclosure, the k-space interpolation is performed by the linear phase interpolation and non-linear magnitude interpolation. FIG. 5A1 depicts an example of acquired k-space data for parallel imaging with oversampling k-space data. k-space data 580 includes partial under-sampled k-space data 562, partial fully-sampled k-space data 564, and partial under-sampled k-space data 566. All of the partial fully-sampled k-space data 564 is fully acquired. The partial under-sampled k-space data 562 and the partial under-sampled k-space data 566 include missing k-space lines. For example, the partial under-sampled k-space data 562 includes acquired k-space lines 572-1 and 572-2 and missing k-space lines 574-1, 574-2, 574-3, 574-4.

Each of FIGS. 5A2 and 5A3 depicts an example of a phase and a magnitude of missing k-space data to be interpolated using k-space scaling method, respectively. k-space data 590 is part of k-space data of k-space 562 or 566. The phase of k-space data is assumed to be changed linearly and the phase of the missing k-space data from k-space line (j, k+1) 604-1 to k-space line (j, k+n−1) 604-n−1 can be obtained using the phase of acquired phases of the nearest k-space data:

$$\varphi_{j,k+m} = \varphi_{j,k} + \frac{1}{n}\sum_{m=1}^{n-1}(\varphi_{j,k+n} - \varphi_{j,k}) \quad \text{(Equation 2)}$$

where φ is a phase of k-space data and n (n>1) is an accelerated factor. m represents $m^{th}$ missing k-space data between acquired k-space lines 602-1 (j, k) and 602-2 (j, k+n). $\varphi_{j,k}$ is a phase of k-space data at the location of frequency encoding of j and phase encoding of k (i.e., k-space coordinates).

The magnitude of k-space data can change nonlinearly and given by:

$$A_{j,k+m} = f(A_{j+h,k+l}) \quad \text{(Equation 3)}$$

where 602-h (k+h, :) and 602-1 (j+l, :) (depicted in FIG. 5A3) can be any of acquired k-space data coordinates near the missing k-space data. The relational information f can be determined by Bloch equations and fitting of reference data or oversampled k-space data. In addition, f can be obtained with the objective function to minimize the difference between the first under-sampled k-space lines and the corresponding second partial k-space lines. The relational information may be non-linear complex matrix and the objective function related to image quality (i.e., image artifacts, SNR and sharpness, etc.). As the difference in acquiring the sequence and imaging parameters between the first partial k-space lines and the second partial of k-space lines becomes smaller, the error in parallel imaging reconstruction becomes smaller.

Figure 5B:
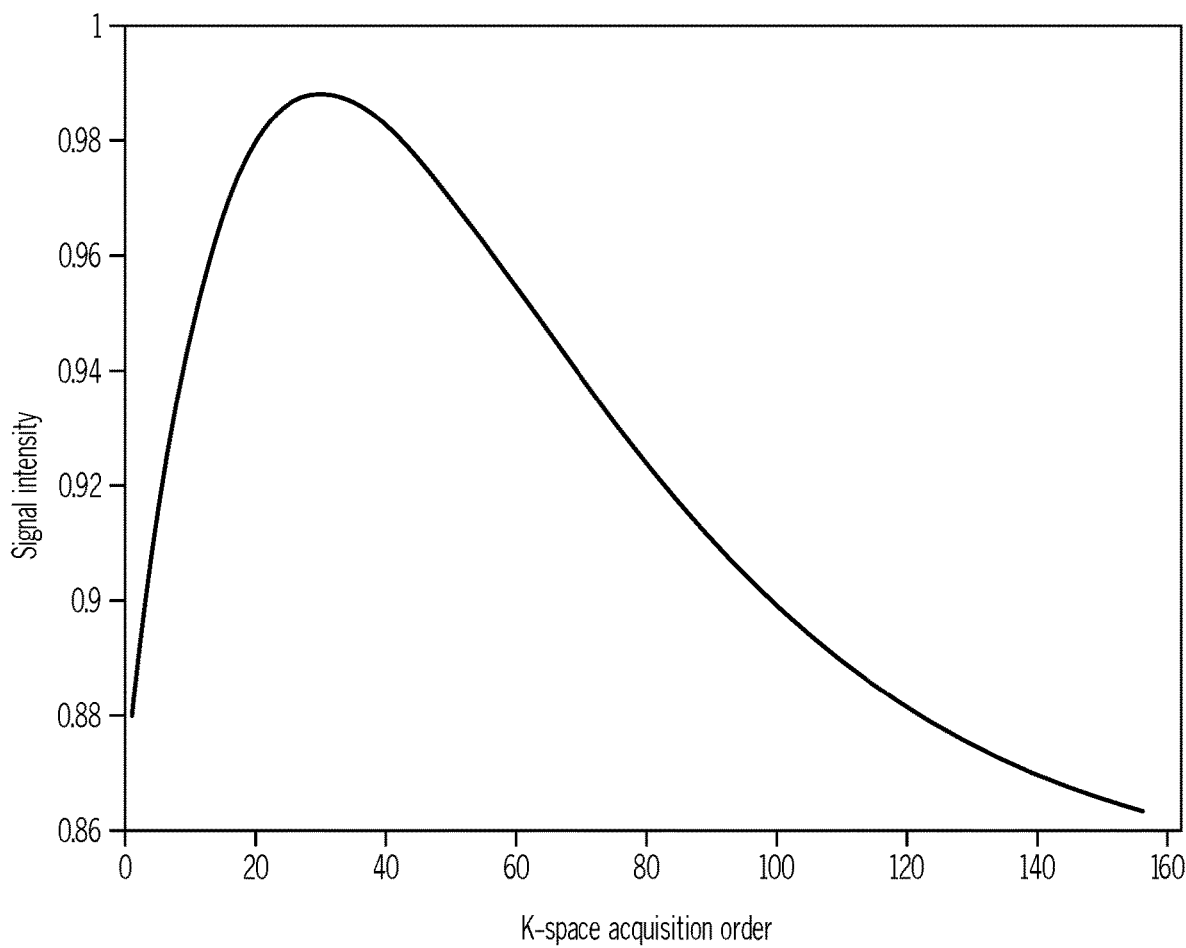
FIG. 5B is a graph showing non-linear relationship between signal intensity and k-space acquisition order according to one example in the present disclosure.

FIG. 5B is a graph illustrating an example operation for showing the non-linear relationship between signal intensity and k-space acquisition order for 3D magnetization-prepared rapid gradient-echo sequence. In FIG. 5B, the simulated signal intensity of brain tissue for different k-space acquisition order for the sequential k-space trajectory at the inversion recovery time of 500 ms and 3.0 Tesla MRI system. $T_1$, $T_2$ and proton density of brain tissue are given 1000 ms, 100 ms, 0.7, respectively. The result suggested that the change in k-space magnitude is non-linear. The non-linear k-space interpolation should be used in parallel imaging reconstruction.

k-space super-resolution method performs an extension of k-space data based on k-space resolution along readout encoding direction that is much higher than its resolution along phase encoding direction. A high resolution k-space data can be obtained by several k-space data with low spatial resolution.

Figure 6:
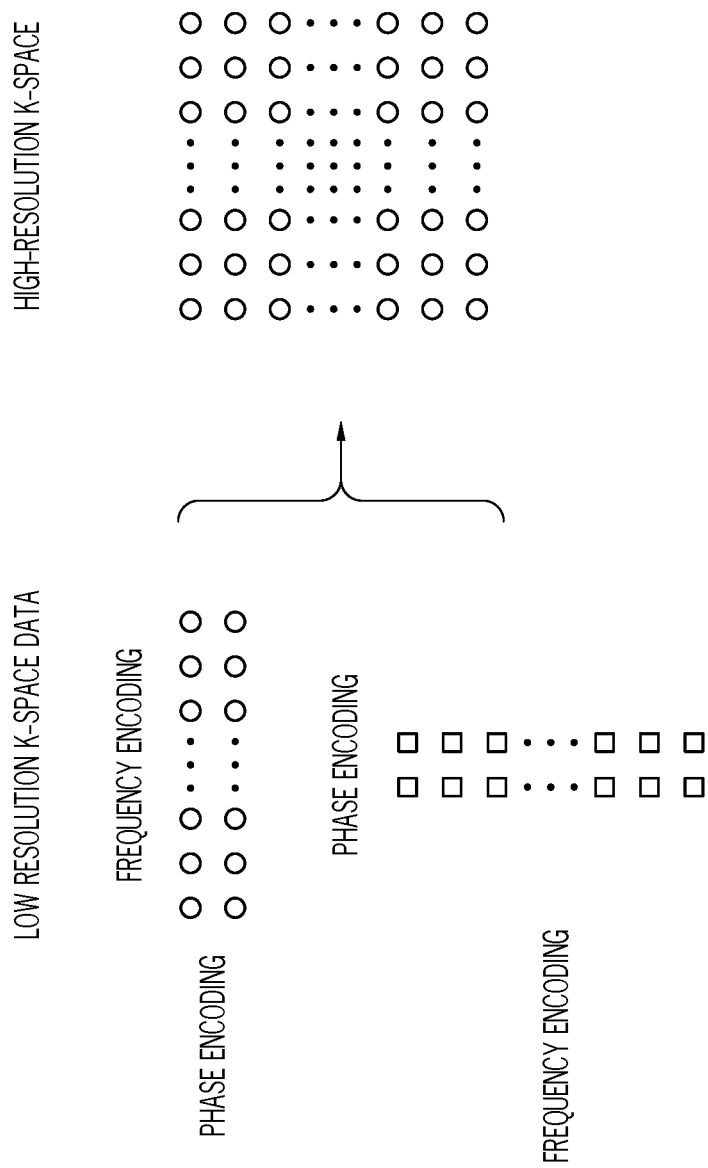
FIG. 6 is a graph illustrating an example operation for a k-space super-resolution method according to one example in the present disclosure.

Super-resolution image is a technique that construct high-resolution images from several low-resolution images, thereby increasing image resolution. The basic idea of super-resolution image is to combine the non-redundant information contained in multiple low-resolution images to create a high-resolution image. Additionally, priori-information-based approaches have been used for super-resolution MRI. A 3D super-resolution MRI is obtained for fusing orthogonally acquired MRI scans or different spatial orientations. Though super-resolution technique has been widely used in image domain, it has not been used in k-space domain. In the present disclosure, the super-resolution k-space method may be used for k-space interpolation in parallel imaging reconstruction. FIG. 6 is a graph illustrating an example operation for k-space super-resolution method according to one example in the present disclosure. Since k-space resolution along readout encoding direction is much higher than its resolution along phase encoding direction, a high resolution k-space data can be obtained by two k-space data which frequency encoding orthogonally oriented with one another.

According to iterative k-space reconstruction method, missing k-space lines can be initially replaced with a zero-filling. Another approach is to estimate the missing space data by iteratively applying complex correction and acquired the nearest neighbor k-space data. Details of iterative k-space reconstruction method will be described below with reference to FIG. 7.

Referring back to FIG. 2, in step 240, the computing device 100 recovers respectively missing k-space lines of each of the set of first under-sampled k-space data using corresponding second partial or fully-sampled k-space data and corresponding first under-sampled k-space data. For example, for the first under-sampled k-space data 310-1, the computing device 100 recovers missing k-space lines 320-1. Similarly, for the first under-sampled k-space data 310-2, the computing device 100 recovers missing k-space lines 320-2. For the first under-sampled k-space data 310-3, the computing device 100 recovers missing k-space lines 320-3. For the first under-sampled k-space data 310-4, the computing device 100 recovers missing k-space lines 320-4.

Figure 4:
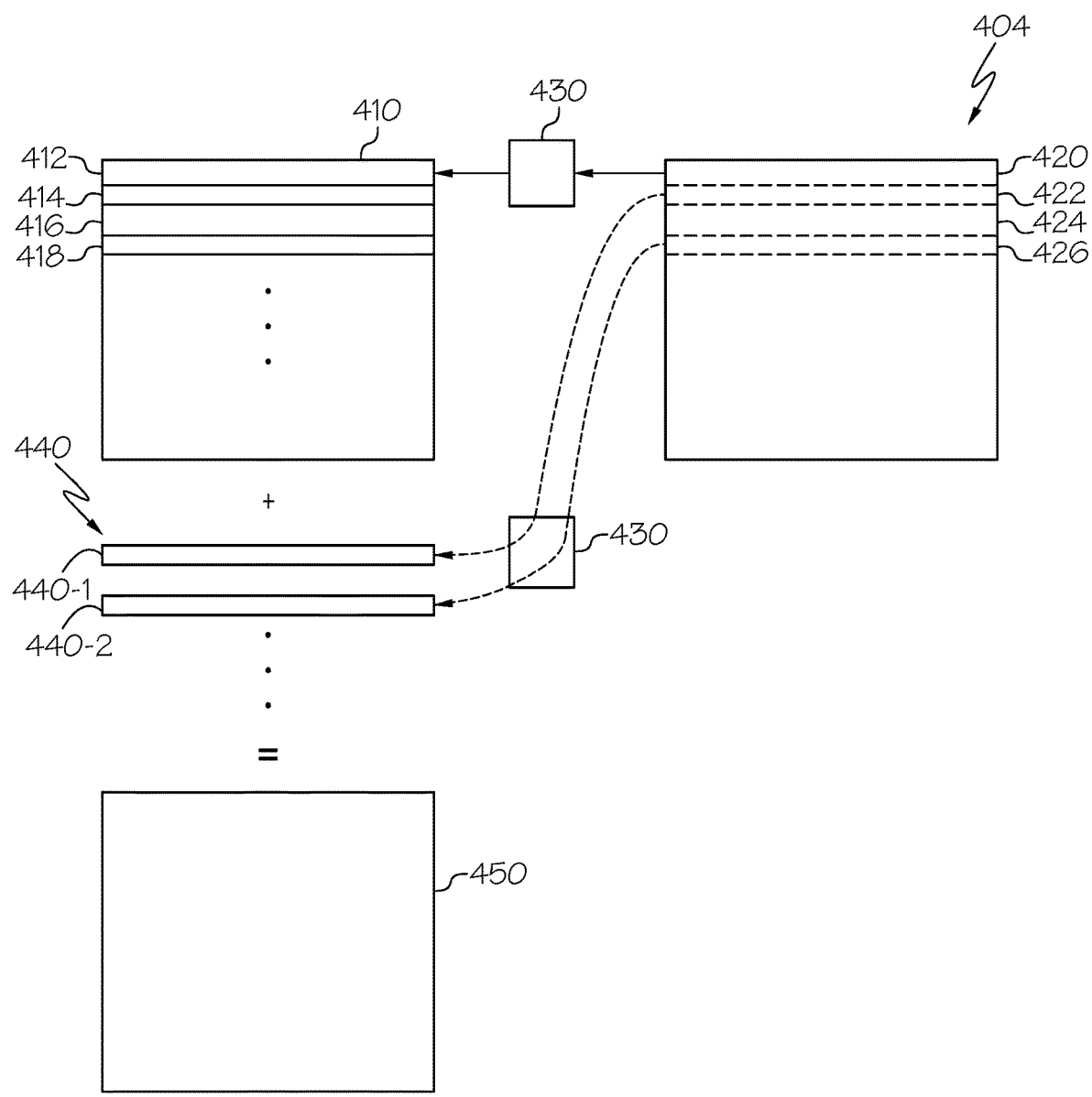
FIG. 4 is a schematic diagram illustrating recovery of missing k-space lines of under-sampled k-space data according to examples in the present disclosure.

In embodiments, the computing device 100 recovers the missing k-space lines of the first under-sampled k-space data based on a transformation matrix defining transformation between the second partial or fully-sampled k-space data and the first under-sampled k-space data. By referring to FIG. 4, the first under-sampled k-space data 410 may correspond to one of the first under-sampled k-space data 310-1, 310-2, 310-3, 310-4. k-space lines 414, 418, and so on are missing due to parallel MR imaging. The computing device 100 may interpolate corresponding second partial or fully sampled k-space data to obtain interpolated second partial or fully-sampled k-space data 404. The resolution of the interpolated second partial or fully-sampled k-space data 404 may match with the resolution of the first under-sampled k-space data acquired by each of the plurality of receiver coils respectively.

The computing device 100 may estimate the transformation matrix based on the first under-sampled k-space data and the interpolated second partial or fully-sampled k-space data respectively. By referring to FIG. 4, the transformation matrix 430 may be estimated based on k-space data 420 of the interpolated second partial or fully-sampled k-space data 404 and k-space data 412 of the first under-sampled k-space data 410. The transformation matrix may be estimated from at least one of phase, magnitude, real, and imaginary of the interpolated second partial or fully sampled k-space data 404 and the first under-sampled k-space data 410. The transformation matrix in k-space domain may include, but not limited to, at least one of an affine transform matrix, a rigid transform matrix, a linear transform matrix, a non-linear transform, and a non-rigid transform matrix.

Then, the computing device 100 determines the missing k-space lines of the first under-sampled k-space data based on the estimated transformation matrix and the interpolated second partial or fully-sampled k-space data corresponding to the missing k-space lines of the first under-sampled k-space data respectively. For example, the computing device 100 recovers the missing k-space line 440-1 based on the estimated transformation matrix 430 and k-space data 422 of the interpolated second partial or fully-sampled k-space data. Similarly, the computing device 100 recovers the missing k-space line 440-2 based on the estimated transformation matrix 430 and k-space data 426 of the interpolated second partial or fully-sampled k-space data. The recovered missing k-space lines 440 may be combined with the first under-sampled k-space data 410 to constitute a full k-space dataset 450.

In some embodiments, the computing device 100 recovers the missing k-space lines of the first under-sampled k-space data based on relational information. For example, the computing device 100 estimates relational information between a k-space line of the interpolated second partial or fully-sampled k-space data and another k-space line adjacent to the k-space line. Then, the computing device 100 synthesizes the missing k-space lines of the first under-sampled k-space data based on the k-space lines of the acquired first under-sampled k-space data adjacent to the missing k-space lines and the relational information.

In step 250, the computing device 100 forms a plurality of full k-space datasets related to the target area by respectively combining each of the set of first under-sampled k-space data and corresponding recovered missing k-space lines for each of the plurality of receiver coils. By referring to FIG. 3, the computing device 100 forms a full k-space dataset 330-1 by combining the first under-sampled k-space data 310-1 and the recovered missing k-space lines 320-1. Similarly, the computing device 100 forms a full k-space dataset 330-2 by combining the first under-sampled k-space data 310-2 and the recovered missing k-space lines 320-2. The computing device 100 forms a full k-space dataset 330-3 by combining the first under-sampled k-space data 310-3 and the recovered missing k-space lines 320-3. The computing device 100 forms a full k-space dataset 330-4 by combining the first under-sampled k-space data 310-4 and the recovered missing k-space lines 320-4.

In some embodiments, the computing device 100 may form a plurality of full k-space dataset related to the target area by performing k-space interpolation of the set of the first under-sampled k-space data without conducting the steps 240 and 250 above. For example, interpolation of the set of the first under-sampled k-space data may recover full missing k-space lines of each of the first under-sampled k-space data to form a plurality of full k-space datasets related to the plurality of receiver coils. In some embodiments, the recovered missing k-space lines of each of the set of the first under-sampled k-space data may be corrected by a mathematic relationship (such as a rational information or a transformation matrix) that is obtained based on the acquired first under-sampled k-space data and corresponding second partial or fully sampled k-spaced data.

In step 260, the computing device 100 obtains a plurality of fully-sampled images from the plurality of full k-space datasets corresponding to the plurality of receiver coils. By referring to FIG. 3, the computing device 100 may obtain a plurality of fully-sampled images 340-1, 340-2, 340-3, 340-4 from the plurality of full k-space datasets 330-1, 330-2, 330-3, 330-4.

In step 270, the computing device 100 combines images of each individual coils into a final image. By referring to FIG. 3, the computing device 100 may combine the images 340-1, 340-2, 340-3, 340-4 into a final image 350.

In this disclosure, the missing k-space data of a receive coil is recovered by the acquired k-space data of the receive coil and reference data. The recovered missing k-space is independent of the acquired k-space data of other receive coils.

Figure 7:
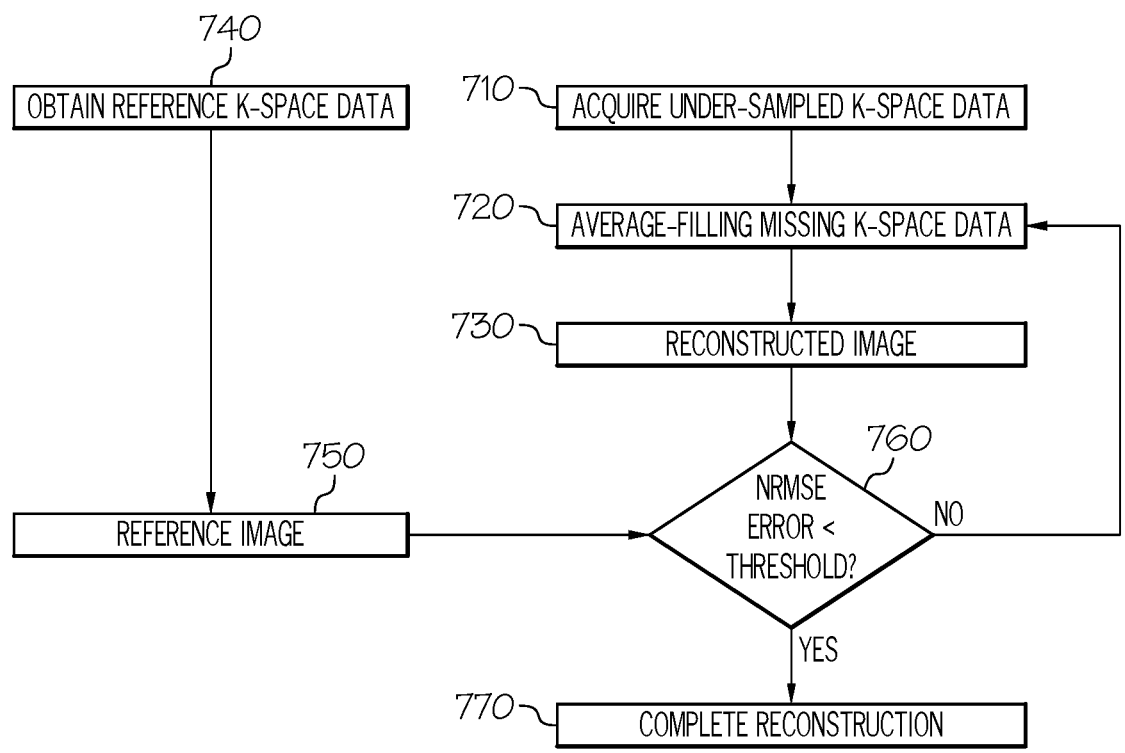
FIG. 7 is a flowchart illustrating an example operation for an iterative k-space reconstruction method according to one example in the present disclosure.

FIG. 7 is a flowchart illustrating an example operation for iterative k-space reconstruction method.

In step 710, under-sampled k-space data is acquired using parallel MR imaging. In step 720, initial phase and magnitude of missing k-space data is filled by uniform phase steps and magnitude steps of the nearest two acquired k-space data. For example, if there exists one missing k-space line between two acquired k-space lines when the accelerated factor equals to 2, the phase step (or phase increment) is a half of phase difference of the two acquired k-space. If the accelerated factor is n, the phase step (or phase increment) is one $n^{th}$ of phase difference of the two acquired k-space. Similarly for magnitude of the missing k-space can be synthesized.

In step 730, a reconstructed image is produced by a Fourier transform in a receiver coil. In step 740, reference k-space data, i.e., full-sampled k-space data is obtained. In step 750, a reference image is obtained by the Fourier transform of the fully-sampled k-space data. The steps 740 and 750 may be conducted in parallel with steps 710, 720, or 730.

In step 760, it is determined whether NRMSE error is less than a threshold value. If the NRMSE error is less than the threshold value, the reconstruction is completed in step 770. If the NRMSE error is not less than the threshold value, the process returns to step 720 and phase and magnitude of the missing k-space is replaced with the averaged phase and magnitude of the two nearest synthesized k-space data. The iterative reconstruction procedure is conducted until NRMSE error is less than the threshold value.

For high accelerations, combinations of partial-Fourier like trajectories with lower parallel accelerations, using constrained reconstruction or the homodyne algorithm, generally performed better than constrained reconstruction with regular under-sampling and larger parallel acceleration. Conventional parallel imaging with partial Fourier techniques suffer from both phase artifacts caused by partial Fourier and high noise amplification caused by parallel imaging. There are many reasons to consider combining partial Fourier and parallel MR imaging for reducing imaging time and the spatial resolution of single-shot imaging.

Figure 8:
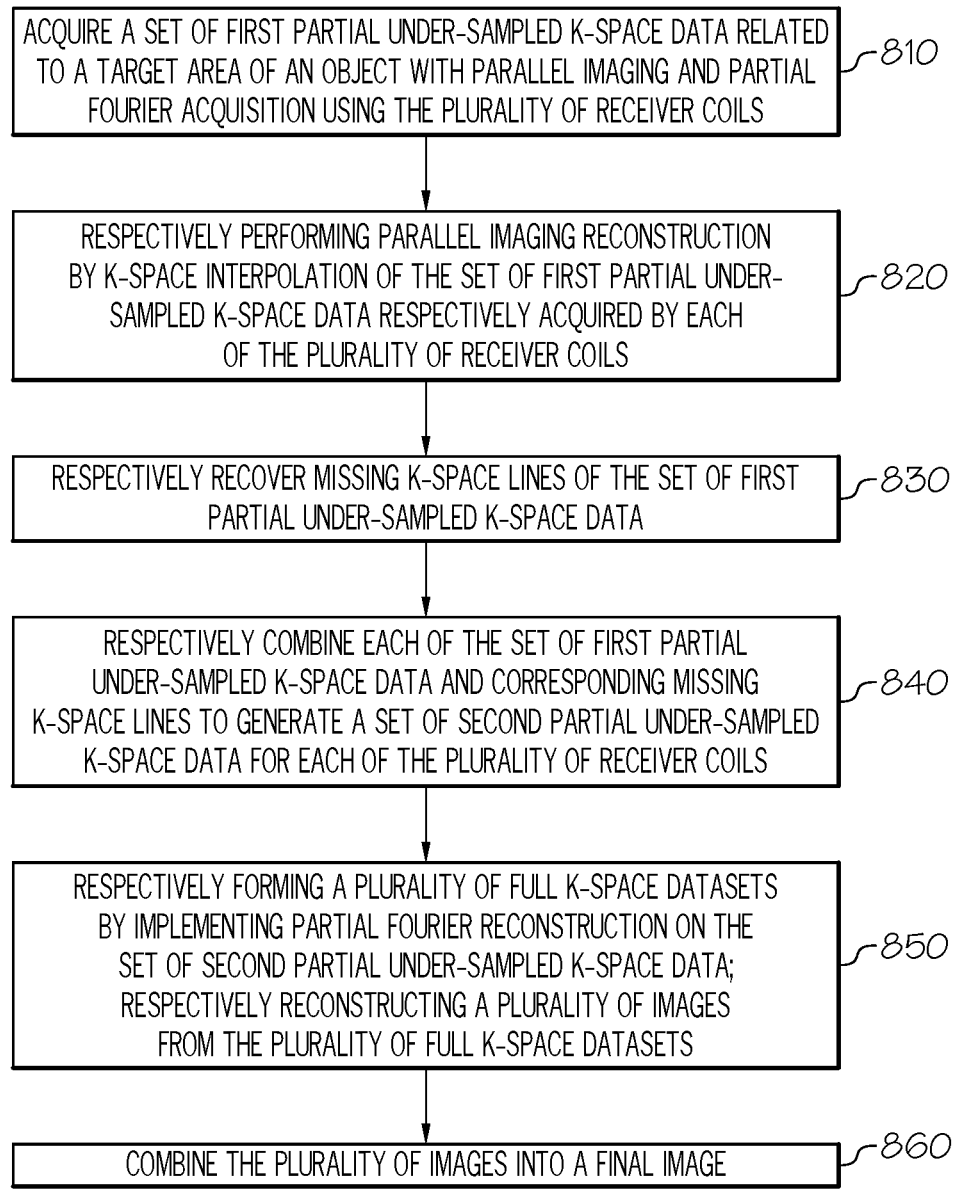
FIG. 8 is a flowchart for reconstructing images acquired with both parallel imaging and partial Fourier acquisition technique for each receiver coil or coil element according to one example in the present disclosure.

FIG. 8 is a graph illustrating an example operation reconstructing the images acquired with both parallel imaging and partial Fourier acquisition technique for each receiver coil or coil element according to one example in the present disclosure.

Figure 10:
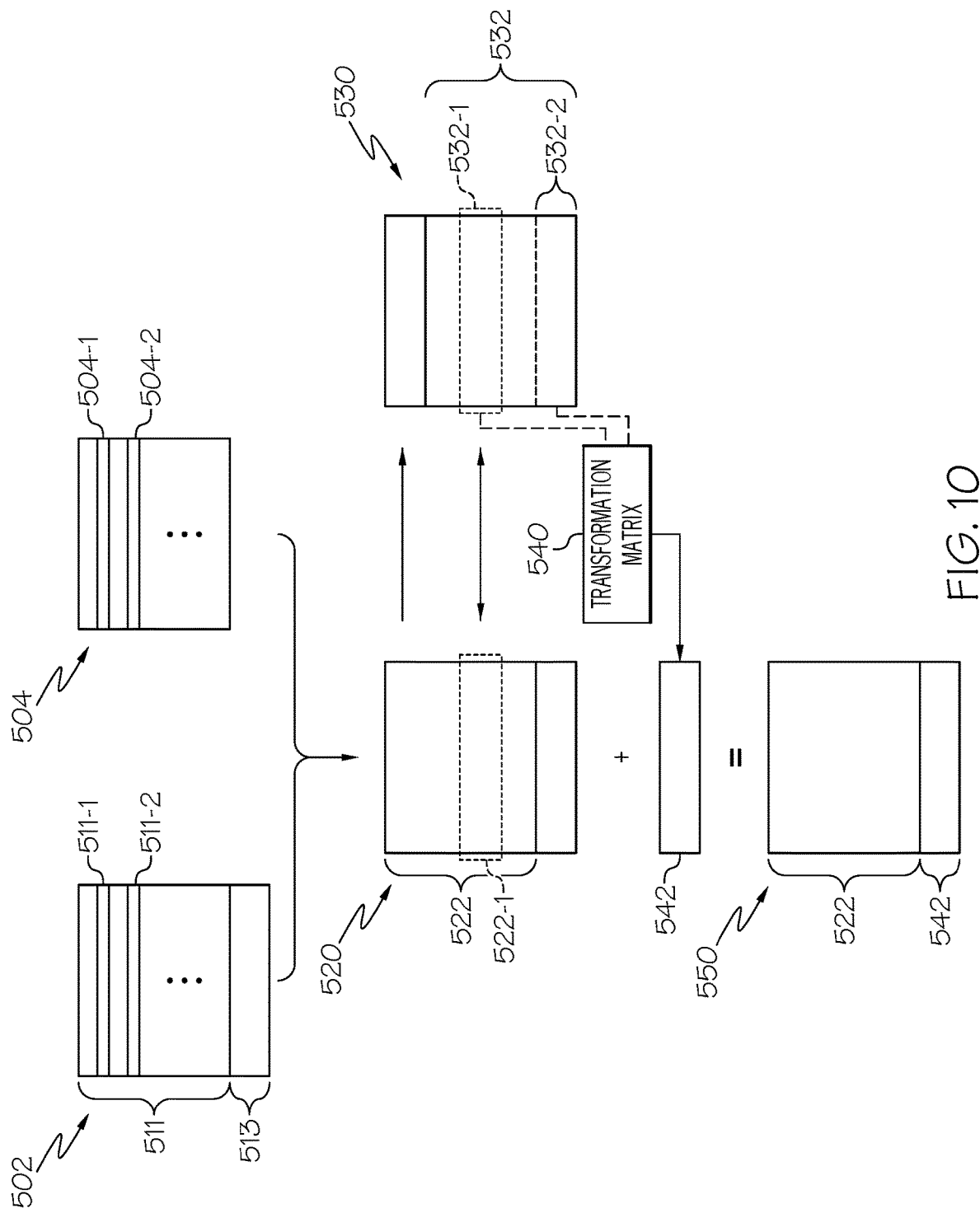
FIG. 10 is a schematic diagram illustrating the partial Fourier reconstruction according to one example in the present disclosure.

In step 810, the computing device 100 acquires a set of first partial under-sampled k-space data related to a target area of an object with parallel imaging and partial Fourier acquisition using the plurality of receiver coils. For example, the computing device 100 acquires a set of first partial under-sampled k-space data related to a target area of an object with parallel imaging and partial Fourier acquisition using the plurality of receiver coils 40-1, 40-2, 40-3, and 40-4 in FIG. 3. Referring to FIG. 10, the first partial under-sampled k-space data 502 can be obtained from one of the plurality of receiver coils 40-1, 40-2, 40-3, and 40-4. The computing device 100 may obtain a set of first partial under-sampled k-space data respectively corresponding to the plurality of receiver coils 40-1, 40-2, 40-3, and 40-4. In embodiments, the first partial under-sampled k-space data may be acquired in at least one of phase-encoding and frequency-encoding direction.

The first partial under-sampled k-space data 502 may include missing k-space lines such as missing k-space lines 511-1 and 511-2 due to parallel MR imaging. In addition, the first partial under-sampled k-space data 502 is partial k-space data, e.g., as shown in the partial k-space dataset 511 in FIG. 10. Without loss of the generality, fully sampled 2D k-space data are to be set as $S(k_x, k_y)$, where $k_x$ and $k_y$ belongs to the full sampling range $[-k_{max}, k_{max}]$. As shown in the first partial under-sampled k-space data 502, partial Fourier acquired data $S_{acquired}(k_x, k_y)$ ($k_x \in [-k_{max}, k_{max}]$ and $k_y \in [-k_N, k_{max}]$) are sampled only over the positive spatial frequencies plus a narrow band of low negative spatial frequencies along a phase encoding direction (y direction), where $k_N < k_{max}$. The portion 513 represents portion where k-space data is not acquired by the MRI scanner.

In step 820, the computing device 100 respectively performs parallel imaging reconstruction by k-space interpolation of the set of first partial under-sampled k-space data respectively acquired by each of the plurality of receiver coils.

In step 830, the computing device 100 respectively recover missing k-space lines of the set of first partial under-sampled k-space data. By referring to FIG. 10, for example, the computing device 100 recovers missing k-space data 504 which includes missing k-space lines 504-1, 504-2, and so on. The missing k-space data 504 may be obtained in a similar way as described above with reference to FIG. 2. The computing device 100 may recover missing k-space lines of the set of first partial under-sampled k-space data respectively corresponding to the plurality of receiver coils 40-1, 40-2, 40-3, and 40-4. In some embodiments, the missing k-space data caused by parallel imaging acquisition further may be obtained or recovered using algorithms in image domain, such as SENSE or using algorithms in k-space domain, such as GRAPPA.

In step 840, the computing device 100 respectively combines each of the set of first partial under-sampled k-space data and corresponding missing k-space lines to generate a set of second partial under-sampled k-space data for each of the plurality of receiver coils. For example, for the receiver coil 40-1 in FIG. 3, the computing device 100 combines the first partial under-sampled k-space data 502 and recovered missing k-space lines 504 to generate second partial under-sampled k-space data 520. The second partial under-sampled k-space data 520 is partial k-space data, e.g., as shown in the partial k-space dataset 522 in FIG. 10. The portion 523 represents portion where k-space data is not acquired by the MRI scanner. Similarly, for other receiver coils such as the receiver coils 40-2, 40-3, 40-4, the computing device 100 respectively combines each of the set of first partial under-sampled k-space data and corresponding missing k-space lines to generate a set of second partial under-sampled k-space data.

In step 850, the computing device 100 respectively forms a plurality of full k-space datasets by implementing partial Fourier reconstruction on the set of second partial under-sampled k-space data. For example, the computing device 100 forms a full k-space dataset 550 by implement partial Fourier reconstruction on the second partial under-sampled k-space data 520 related to the receiver coil 40-1. Similarly, for other receiver coils such as the receiver coils 40-2, 40-3, 40-4, the computing device 100 respectively forms a plurality of full k-space datasets by implementing partial Fourier reconstruction on the set of second partial under-sampled k-space data. The details of partial Fourier reconstruction will be described below with reference to FIG. 9.

In step 860, the computing device 100 respectively reconstructs a plurality of images from the plurality of full k-space datasets. For example, the computing device 100 may reconstruct an image from the full k-space dataset 550 related to the receiver coil 40-1. Similarly, for other receiver coils such as the receiver coils 40-2, 40-3, 40-4, the computing device 100 respectively reconstructs a plurality of images from the plurality of full k-space datasets.

In step 870, the computing device 100 combines the plurality of images into a final image. For example, similar to combining the fully sampled images 340-1, 340-2, 340-3, 340-4 to form a final image 350 in FIG. 3, the computing device 100 combines the plurality of images obtained in step 860 into a final image.

Figure 9:
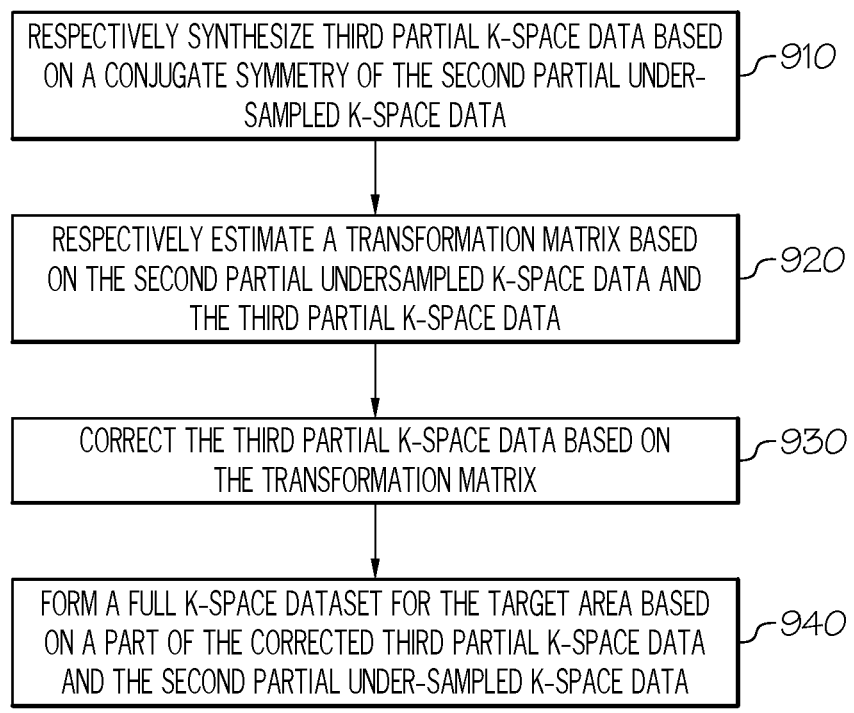
FIG. 9 is a flowchart for forming a full k-space data by the partial Fourier reconstruction according to one example in the present disclosure.

FIG. 9 is a graph illustrating for forming a full k-space data by the partial Fourier reconstruction according to one example in the present disclosure.

In step 910, the computing device 100 respectively synthesizes third partial k-space data based on a conjugate symmetry of the second partial under-sampled k-space data. For example, by referring to FIG. 10 the computing device 100 synthesizes the third partial k-space data 530 based on a conjugate symmetry of the second partial under-sampled k-space data 520 related to the receiver coil 40-1. Similarly, for other receiver coils such as the receiver coils 40-2, 40-3, 40-4, the computing device 100 synthesizes third partial k-space data based on a conjugate symmetry of each of the second partial under-sampled k-space data respectively related to the receiver coils 40-2, 40-3, 40-4.

In step 920, the computing device 100 respectively estimates a transformation matrix based on the second partial under-sampled k-space data and the third partial k-space data. The transformation matrix may be a multiple dimensional matrix. The transformation matrix is configured to correct translation, rotation, scaling and shearing of an entire or part of k-space dataset. By referring to FIG. 10, the computing device 100 may estimate a transformation matrix 540 based on the second partial under-sampled k-space data 520 related to the receiver coil 40-1 and the third partial k-space data 530. Specifically, the computing device 100 may estimate the transformation matrix 540 based on k-space data 522-1 of the second partial under-sampled k-space data 520 and k-space data 532-1 of the third partial k-space data 530. Similarly, for other receiver coils such as the receiver coils 40-2, 40-3, 40-4, the computing device 100 estimates a transformation matrix based on the second partial under-sampled k-space data related to corresponding receiver coil and the third partial k-space data.

In step 930, the computing device 100 corrects the third partial k-space data based on the transformation matrix. For example, by referring to FIG. 10, k-space data 532-2 of the third partial k-space data 530 corresponds to the portion 523 of the second partial under-sampled k-space data 520 related to the receiver coil 40-1 in FIG. 3. The computing device 100 corrects the k-space data 532-2 based on the transformation matrix 540. Specifically, the transformation matrix 540 receives the k-space data 532-2 as an input and outputs corrected k-space data 542 as an output. Similarly, for other receiver coils such as the receiver coils 40-2, 40-3, 40-4, the computing device 100 corrects third partial k-space data based on the transformation matrix related to corresponding receiver coil 40-2, 40-3, or 40-4.

In step 940, the computing device 100 forms a full k-space dataset for the target area based on a part of the corrected third partial k-space data and the second partial under-sampled k-space data 520. For example, by referring to FIG. 10, the computing device 100 forms a full k-space dataset 550 by combining the second partial under-sampled k-space data 520 and the corrected third partial k-space data 542 both of Which are related to the receiver coil 40-1. Similarly, for other receiver coils such as the receiver coils 40-2, 40-3, 40-4, the computing device 100 forms a full k-space dataset for the target area based on a part of the corrected third partial k-space data and the second partial under-sampled k-space data 520.

It should be understood that the above-described subject matter may also be implemented as a computer-controlled apparatus, a computer process, a computing system, or an article of manufacture, such as a computer-readable storage medium. It should be understood that the obtained method can be easily extended to correct similar k-space artifacts caused in other sequences that are not echo-planar-imaging based sequences.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

In some embodiments, implementation of the disclosed methods may include generating one or more web pages for facilitating input, output, control, analysis, and other functions. In other embodiments, the methods may be implemented as a locally-controlled program on a local computer system which may or may not be accessible to other computer systems. In still other embodiments, implementation of the methods may include generating and/or operating modules which provide access to portable devices such as laptops, tablet computers, digitizers, digital tablets, smart phones, and other devices.

What is claimed is:

1. A method for reconstructing a full k-space dataset using parallel magnetic resonance (MR) imaging technique, the method comprising:

acquiring, by a plurality of receiver coils, a set of first under-sampled k-space data related to a target area of an object respectively corresponding to the plurality of receiver coils;

receiving a set of second partial or fully-sampled k-space data related to the target area respectively corresponding to the set of first under-sampled k-space data;

respectively performing k-space interpolation of the set of the first under-sampled k-space data respectively acquired by each of the plurality of receiver coils;

recovering respectively missing k-space lines of each of the set of first under-sampled k-space data using corresponding second partial or fully-sampled k-space data and corresponding first under-sampled k-space data;

forming a plurality of full k-space datasets related to the target area by respectively combining each of the set of first under-sampled k-space data and corresponding recovered missing k-space lines for each of the plurality of receiver coils;

obtaining a plurality of fully-sampled images from the plurality of full k-space datasets corresponding to the plurality of receiver coils; and combining images of each individual coils into a final image.

2. The method of claim 1, wherein the second partial or fully-sampled k-space data of the target area is obtained by:
   oversampling a part of missing k-space data of the first under-sampled k-space data acquired by corresponding receiver coil or coils to generate an artifact-free k-space data as a reference;
   acquiring a fully sampled MRI k-space data acquired by corresponding receiver coil or coils; or
   implementing Fourier transform of an artifact-free image in image domain.

3. The method of claim 2, wherein the fully sampled MRI k-space data is acquired using imaging parameters that are substantially the same as imaging parameters used for acquiring the first under-sampled k-space data.

4. The method of claim 1, wherein the k-space interpolation is performed by:
   a k-space scaling method; or
   a super-resolution k-space method; or
   an iterative k-space reconstruction method.

5. The method of claim 1, wherein recovering respectively the missing k-space lines of the first under-sampled k-space data using the second partial or fully-sampled k-space data and corresponding first under-sampled k-space data further comprises:
   recovering the missing k-space lines of the first under-sampled k-space data based on a transformation matrix defining transformation between the second partial or fully-sampled k-space data and the first under-sampled k-space data; or
   recovering the missing k-space lines of the first under-sampled k-space data based on relational information.

6. The method of claim 5, wherein recovering the missing k-space lines of the first under-sampled k-space data based on the transformation matrix comprises:
   interpolating the second partial or fully sampled k-space data such that a resolution of the interpolated second partial or fully sampled k-space matches with a resolution of the first under-sampled k-space data acquired by each of the plurality of receiver coils respectively;
   estimating the transformation matrix based on the first under-sampled k-space data and the interpolated second partial or fully-sampled k-space data respectively; and
   determining the missing k-space lines of the first under-sampled k-space data based on the estimated transformation matrix and the interpolated second partial or fully-sampled k-space data corresponding to the missing k-space lines of the first under-sampled k-space data respectively.

7. The method of claim 6, wherein the transformation matrix represents variations of translation, rotation and/or shear data of k-space data.

8. The method of claim 5, wherein recovering the missing k-space lines of the first under-sampled k-space data based on relational information comprises:
   interpolating the second partial or fully-sampled k-space data such that a resolution of the interpolated second partial or fully sampled k-space data matches with a resolution of the first under-sampled k-space data acquired by the receiver coil;
   estimating relational information between a k-space line of the interpolated second partial or fully-sampled k-space data and another k-space line adjacent to the k-space line; and
   synthesizing the missing k-space lines of the first under-sampled k-space data based on the k-space lines of the acquired first under-sampled k-space data adjacent to the missing k-space lines and the relational information.

9. The method of claim 7, wherein interpolating the second partial or fully-sampled k-space data comprises:
   interpolating a phase of the second partial or fully-sampled k-space data based on a linear relationship of the phase; and
   interpolating a magnitude of the second partial or fully-sampled k-space data based on a non-linear relationship of the magnitude.

10. The method of claim 9, where the non-linear relationship of the magnitude is determined based on Bloch equations of acquiring the second partial or fully-sampled k-space data.

11. The method of claim 1, wherein the k-space data is acquired at least one of rectilinear, echo planar, radial, Cartesian, non-Cartesian, Zig-Zag, stochastic, rosette, TWIRL, WHIRL and spiral trajectories.

12. A magnetic resonance imaging (MRI) method for reconstructing images acquired with both parallel imaging and partial Fourier acquisition technique using a plurality of receiver coils, the method comprising:
   acquiring a set of first partial under-sampled k-space data related to a target area of an object with parallel imaging and partial Fourier acquisition using the plurality of receiver coils;
   respectively performing parallel imaging reconstruction by k-space interpolation of the set of first partial under-sampled k-space data respectively acquired by each of the plurality of receiver coils;
   recovering respectively missing k-space lines of the set of first partial under-sampled k-space data;
   respectively combining each of the set of first partial under-sampled k-space data and corresponding missing k-space lines to generate a set of second partial under-sampled k-space data for each of the plurality of receiver coils;

respectively forming a plurality of full k-space datasets by implementing partial Fourier reconstruction on the set of second partial under-sampled k-space data;
respectively reconstructing a plurality of images from the plurality of full k-space datasets; and
combining the plurality of images into a final image.

13. The method of claim 12, wherein recovering respectively missing k-space lines of the first partial under-sampled k-space data comprises:
recovering the missing k-space lines using algorithms in image domain including SENSE; or
recovering the missing k-space lines using algorithms in k-space domain including GRAPPA.

14. The method of claim 12, wherein respectively forming a plurality of full k-space datasets by implementing the partial Fourier reconstruction comprises:
respectively synthesizing third partial k-space data based on a conjugate symmetry of the second partial under-sampled k-space data;
respectively estimating a transformation matrix based on the second partial under-sampled k-space data and the third partial k-space data;
correcting the third partial k-space data based on the transformation matrix; and
forming a full k-space dataset for the target area based on a part of the corrected third partial k-space data and the second partial under-sampled k-space data.

15. The method of claim 14, wherein respectively estimating a transformation matrix based on the second partial under-sampled k-space data and the third partial k-space data comprises estimating the transformation matrix based on a part of the second partial under-sampled k-space data and a corresponding part of the third partial k-space data.

16. The method of claim 14, wherein the transformation matrix is a multiple dimensional matrix.

17. The method of claim 14, wherein the transformation matrix is configured to correct translation, rotation, scaling and shearing of an entire or part of k-space dataset.

18. A magnetic resonance imaging (MRI) system for parallel imaging reconstruction, the system comprising:
a magnetic field generating unit configured to apply a plurality of RF pulses to a target area of an object;
a plurality of receiver coils configured to receive MR signals from the target area;
a processing unit;
a system memory; and
machine readable instructions stored in the system memory that, when executed by the processing unit, cause the processing unit to:
acquire a set of first under-sampled k-space data related to a target area of an object respectively corresponding to the plurality of receiver coils;
receive a set of second partial or fully-sampled k-space data related to the target area respectively corresponding to the set of first under-sampled k-space data;
perform k-space interpolation of the set of the first under-sampled k-space data respectively acquired by each of the plurality of receiver coils;
recover respectively missing k-space lines of each of the set of first under-sampled k-space data using corresponding second partial or fully-sampled k-space data and corresponding first under-sampled k-space data;
form a plurality of full k-space datasets related to the target area by respectively combining each of the set of first under-sampled k-space data and corresponding recovered missing k-space lines for each of the plurality of receiver coils;
obtain a plurality of fully-sampled images from the plurality of full k-space datasets corresponding to the plurality of receiver coils; and
combine images of each individual coils into a final image.

19. The system of claim 18, wherein the second partial or fully-sampled k-space data of the object is obtained by:
oversampling a part of missing k-space data of the first under-sampled k-space data acquired by corresponding receiver coil or coils to generate an artifact-free k-space data as a reference.

20. The system of claim 18, wherein the second partial or fully-sampled k-space data of the object is obtained by:
acquiring a fully sampled MRI k-space data acquired by corresponding receiver coil or coils; or
implementing Fourier transform of an artifact-free image in image domain.

* * * * *